United States Patent
Tamura et al.

(10) Patent No.: US 10,321,747 B2
(45) Date of Patent: Jun. 18, 2019

(54) MAKEUP ASSISTANCE DEVICE, MAKEUP ASSISTANCE SYSTEM, MAKEUP ASSISTANCE METHOD, AND MAKEUP ASSISTANCE PROGRAM

(71) Applicant: PANASONIC INTELLECTUAL PROPERTY MANAGEMENT CO., LTD., Osaka (JP)

(72) Inventors: Hajime Tamura, Tokyo (JP); Hiroaki Yoshio, Kanagawa (JP); Katsuji Aoki, Kanagawa (JP); Kaori Mori, Kanagawa (JP); Sonoko Hirasawa, Kanagawa (JP); Shin Yamada, Kanagawa (JP); Takayuki Matsukawa, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 409 days.

(21) Appl. No.: 14/764,698

(22) PCT Filed: Nov. 28, 2013

(86) PCT No.: PCT/JP2013/007009
§ 371 (c)(1),
(2) Date: Jul. 30, 2015

(87) PCT Pub. No.: WO2014/118842
PCT Pub. Date: Aug. 7, 2014

(65) Prior Publication Data
US 2015/0366328 A1 Dec. 24, 2015

(30) Foreign Application Priority Data

Feb. 1, 2013 (JP) .................................. 2013-018101
Feb. 1, 2013 (JP) .................................. 2013-018103

(51) Int. Cl.
*A45D 44/00* (2006.01)
*G06T 11/00* (2006.01)
*A61B 5/00* (2006.01)

(52) U.S. Cl.
CPC ........... *A45D 44/005* (2013.01); *A45D 44/00* (2013.01); *G06T 11/00* (2013.01);
(Continued)

(58) Field of Classification Search
CPC .... A45D 44/00; A45D 44/005; A45D 44/007; A45D 2044/007; A61B 5/441;
(Continued)

(56) References Cited

U.S. PATENT DOCUMENTS 6,091,836 A 7/2000 Takano et al.
2007/0172155 A1* 7/2007 Guckenberger .. G06F 17/30247
382/305
(Continued)

FOREIGN PATENT DOCUMENTS

JP 04-279829 10/1992
JP 2003-122825 4/2003
(Continued)

OTHER PUBLICATIONS

U.S. Appl. No. 14/773,476 to Kaori Ajiki et al., filed Sep. 8, 2015.
(Continued)

*Primary Examiner* — Robert P Bullington
(74) *Attorney, Agent, or Firm* — Greenblum & Bernstein, P.L.C.

(57) ABSTRACT

Provided is a cosmetic assist device that can extract a cosmetic technique for making a user's face look like a target face image. The device includes an image capturing unit for capturing a face image of a user, an input unit for inputting a target face image, a synthesized face image generating unit for generating a plurality of synthesized face (Continued)

images obtained by applying mutually different cosmetic techniques on the face image of the user, a similarity determination unit for determining a degree of similarity between each synthesized face image and the target face image, and a cosmetic technique extraction unit for extracting one of the cosmetic techniques that was used to obtain the synthesized face image determined to have a highest degree of similarity by the similarity determination unit.

18 Claims, 14 Drawing Sheets

(52) U.S. Cl.
CPC ...... *A45D 2044/007* (2013.01); *A61B 5/0077* (2013.01); *A61B 5/441* (2013.01)

(58) Field of Classification Search
CPC .. A61B 5/0077; G06K 9/00261; G06T 11/00; G09B 19/00; G09B 19/0023; G09B 19/0076
USPC .......................................................... 434/100
See application file for complete search history.

(56) References Cited

U.S. PATENT DOCUMENTS

| | | | |
|---|---|---|---|
| 2014/0226896 A1* | 8/2014 | Imai | ................ G06Q 50/10 382/154 |
| 2015/0049111 A1 | 2/2015 | Yamanashi et al. | |
| 2015/0050624 A1 | 2/2015 | Yamanashi et al. | |
| 2015/0086945 A1 | 3/2015 | Yamanashi et al. | |
| 2015/0118655 A1 | 4/2015 | Yamanashi et al. | |
| 2015/0248581 A1 | 9/2015 | Gouda et al. | |
| 2015/0254500 A1 | 9/2015 | Izumi et al. | |
| 2015/0254501 A1 | 9/2015 | Yamanashi et al. | |
| 2015/0262403 A1 | 9/2015 | Yamanashi et al. | |

FOREIGN PATENT DOCUMENTS

| | | |
|---|---|---|
| JP | 3408524 | 5/2003 |
| JP | 3614783 | 1/2005 |
| JP | 2006-081847 | 3/2006 |
| JP | 2006-267115 | 10/2006 |
| JP | 2012-008617 | 1/2012 |
| WO | 2008/102440 | 8/2008 |
| WO | 2013/005447 | 1/2013 |

OTHER PUBLICATIONS

U.S. Appl. No. 14/770,167 to Tomofumi Yamanashi et al., filed Aug. 25, 2015.
U.S. Appl. No. 14/774,321 to Kaori Ajiki et al., filed Sep. 10, 2015.
International Search Report issued in PCT/JP2013/007009, dated Feb. 10, 2014.
Office Action issued in European Patent Office (EPO) Counterpart Patent Appl. No. 13873648.3, dated Nov. 9, 2017.
European Search Report in European Patent Application No. 13873648.3, dated Apr. 22, 2016.

* cited by examiner

Fig.8

| age | male | female |
|---|---|---|
| – 20 | • masculine<br>• fresh<br>• boyish | • feminine<br>• cute<br>• innocent |
| 20 – 30 | • masculine<br>• fresh<br>• sharp<br>• wild<br>• cool<br>• intellectual | • feminine<br>• cute<br>• chic<br>• coquette<br>• sexy |
| 30 – | • masculine<br>• sharp<br>• wild<br>• cool<br>• intellectual<br>• dandy | • feminine<br>• sexy<br>• gorgeous<br>• elegant |

[makeup procedure]
1. Apply foundation of FAC1 over the entire face.
2. Draw fine eyebrows with EBC2.
3. Apply fine eye shadow with ESC3.
4. Apply eye line with ILC3.
5. Apply cheek color of CEC4 over the entire cheeks.
6. Apply lipstick of LPC4.

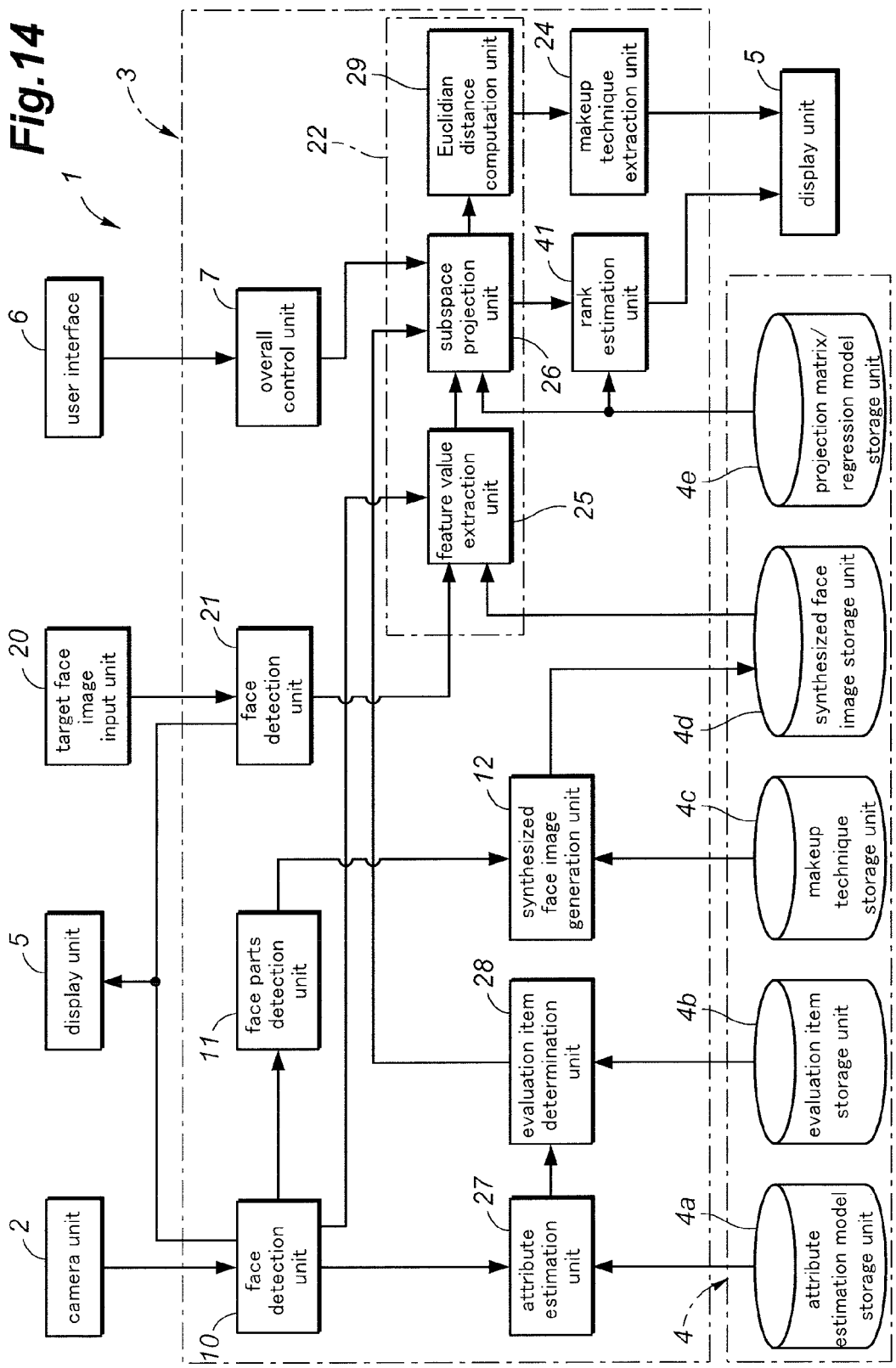

MAKEUP ASSISTANCE DEVICE, MAKEUP ASSISTANCE SYSTEM, MAKEUP ASSISTANCE METHOD, AND MAKEUP ASSISTANCE PROGRAM

TECHNICAL FIELD

The present invention relates to a cosmetic assist device, a cosmetic assist system, a cosmetic assist method and a cosmetic assist computer program that can be used for providing advice on cosmetic procedures to users such as those to whom the cosmetic procedures are to be applied.

BACKGROUND ART

In recent years, cosmetic products have come to range more widely than ever before both in terms of kinds and modes of use. Cosmetic products are now being sold in larger scales than ever before at supermarkets and convenience stores in addition to more conventional sales places where face to face selling is being conducted, and a wide range of cosmetic products are now available to the consumers in larger volumes. The consumer normally obtains information on the cosmetic products and the associated make-up techniques on such products from the documentations attached to the products, magazines and the Internet to make use of such information when applying the cosmetic product on her (or him). However, it is not possible to accurately predict if the result of applying the particular cosmetic product on the user is going to be satisfactory or not merely from such information.

To overcome such a problem of the prior art, Patent Document 1 discloses a method that includes the steps of identifying a cosmetic procedure from a sample image depicting a face which the user desires, applying the identified cosmetic procedure to the face image of the user to generate a reference make-up face image, evaluating a correlation between the face image of the user and the reference make-up face image at each step of the make-up procedure, and providing cosmetic advice based on the result of the evaluating step.

Patent Document 2 discloses an arrangement for extracting two independent feature values (indices regarding how centrifugal or centripetal certain facial parts such as eyes and a nose are, and how linear or curved the shape of each face part is), and classifying the face in terms of the features or impressions thereof depending on which of the four quadrants of a two dimensional evaluation coordinate plane the feature values are plotted in.

PRIOR ART DOCUMENT(S)

Patent Document(s)

Patent Document 1: JP3408524B
Patent Document 2: JP3614783B

SUMMARY OF THE INVENTION

Task to be Accomplished by the Invention

According to the technology disclosed in Patent Document 1, the face of the user may be made look similar to the sample face image (the face image given as the intended result of the selected cosmetic procedure which is referred to as "target face image" hereinafter) by applying the cosmetic procedure determined from the target face image only if the overall appearance of the target face image, the shapes of the parts (face parts) such as the eyes and the nose that constitute the face and the relative positions of these face parts are similar to those of the user (as in the case of identical twins). However, in reality, if the face of the user is significantly different from the target face image, applying the same cosmetic procedure to the face of the user normally does not produce a same result. In particular, in such approaches, because human impressions are not accounted for in the evaluation process, even when a same cosmetic procedure in terms of shape and color is applied to the user, the final result may significantly differ from the target face image in impression (because the similarity in the two faces may fairly poor in human perception). It is extremely difficult to objectively quantize human impressions. Therefore, some trial and error efforts are required in order to achieve a "cute" and other human impressions carried by the target face image in the face of the user.

In Patent Document 1, it is necessary to identify the make-up procedure from the target face image. However, the variety of cosmetic products is so great that it is practically impossible to identify the make-up procedure from the image information alone.

According to the technology disclosed in Patent Document 2, the subject is classified in terms of features and impressions, but it provides nothing more than a general idea as to how the cosmetic procedure should be carried out. Such information on the general idea as to the recommended cosmetic procedure may be beneficial for beauticians who are capable of freely applying different make-up procedures according to the different facial features of the subjects. However, for a common user, even when general information such that the layout of the facial parts should be more centrifugal and the shapes of the face parts should be more curved in order to achieve a feminine look, it is still extremely difficult to determine if a human impression factor such as "feminine look" has been achieved by the given cosmetic procedure and how well it has been achieved.

According to Patent Document 2, the facial features are classified into four quadrants, and a certain human impression is assigned to each quadrant, but the range of human impressions contained in each quadrant is extremely wide. Therefore, even when the technology of Patent Document 2 is applied to machine learning, and the human impression assigned to each quadrant is learnt in terms of evaluation items based on human impressions, those evaluation items that are not required by each particular user are inevitably included in the learning process. For instance, when the user wishes to evaluate the result of a certain cosmetic procedure in terms of evaluation item "cute", the quadrant to which "cute" belongs also includes substantially different evaluation items such as "simple". Therefore, the two faces that may be considered similar as a result of a machine learning process may not be similar in the eyes of the user or the result of the machine learning process may deviate significantly from the human impressions of the user.

The present invention was made in view of such problems of the prior art, and has an object to provide a cosmetic assist device, a cosmetic assist system, a cosmetic assist method and a cosmetic assist computer program that allow a cosmetic procedure for making the face of a user to look very close or similar to the target face image to be extracted in a highly accurate manner, allow the difference between the user's face and the target face image to be displayed in terms of rank values of evaluation items based on human impressions, and allow the user to intuitively evaluate how closely the user's face has been made to look to the target face image as a result of the application of the extracted cosmetic procedure.

Means to Accomplish the Task

The present invention provides a cosmetic assist device, comprising: an image capturing unit for capturing a face image of a user; an input unit for inputting a target face image; a synthesized face image generating unit for generating a plurality of synthesized face images obtained by applying mutually different cosmetic techniques on the face image of the user; a similarity determination unit for determining a degree of similarity between each synthesized face image and the target face image; and a cosmetic technique extraction unit for extracting one of the cosmetic techniques that was used to obtain the synthesized face image determined to have a highest degree of similarity by the similarity determination unit.

Thereby, a more appropriate cosmetic technique can be proposed according to the degree of similarity between the target face image and each synthesized face image obtained by applying a different cosmetic technique on the face image of the user.

The present invention further provides a cosmetic assist device, comprising: an image capturing unit for capturing a face image of a user; an input unit for inputting a target face image; a synthesized face image generating unit for generating a plurality of synthesized face images obtained by applying mutually different cosmetic techniques on the face image of the user; a similarity determination unit for determining a degree of similarity between each synthesized face image and the target face image; an evaluation unit for producing a rank value of a prescribed evaluation item for each of the face image of the user and the target face image; and a display unit for displaying the rank value and one of the cosmetic techniques that was used to obtain the synthesized face image determined to have a highest degree of similarity by the similarity determination unit.

Thereby, according to the degree of similarity between the target face image and each synthesized face image obtained by applying a different cosmetic technique on the face image of the user, a make-up technique that can make the user's face look similar to the target face image can be proposed, and the difference between the user's face and the target face image can be displayed as a numerical value on each evaluation item based on human impressions.

In the cosmetic assist device of the present invention, preferably, the similarity determination unit comprises a feature value extraction unit for extracting a prescribed feature value from each of the target face image and the synthesized face images, and a projection unit for projecting the feature value onto a subspace corresponding to each of a plurality of different evaluation items based on human impressions; and wherein a degree of similarity in each subspace is determined from a Euclidian distance between coordinates onto which the feature values obtained from each synthesized face image and the target face image are projected, and a degree of similarity between the target face image and the synthesized face image is determined according to a degree of similarity associated with each different evaluation item in the subspace.

By using the evaluation items based on human impressions, even when the face of the user and the target face image are fundamentally different, the degree of similarly can be determined in an appropriate manner.

In the cosmetic assist device of the present invention, preferably, the evaluation unit comprises: a feature value extraction unit for extracting a prescribed feature value from the target face image and each of the synthesized face images; a projection unit for projecting the feature values onto a subspace corresponding to each of a plurality of different evaluation items based on human impressions; and a rank estimation unit for producing a rank value of a prescribed evaluation item according to coordinates of feature values projected by the projection unit onto each subspace.

Because the evaluation items based on human impressions are evaluated in terms of rank values, it is possible to evaluate a similarity in terms of human impressions such as "cute" between the user's face image and the target face image with a numerical value.

In the cosmetic assist device of the present invention, preferably, the image capturing unit is configured to capture the face image of the user repeatedly at a prescribed timing, the evaluation unit is configured to produce a rank value for each renewed face image of the user, and the display unit is configured to display each renewed face image of the user and the rank values.

Thus, as the application of the cosmetic technique to the user progresses, the face image of the user and the associated rank values are renewed so that the user is enabled to intuitively determine the progress that has been made with the ongoing cosmetic procedure toward the target face image.

In the cosmetic assist device of the present invention, the display unit may be configured to display the rank values on a radar chart having a plurality of coordinate axes corresponding to the different evaluation items.

By simultaneously displaying the rank values of the user's face image and the target face image with respect to a plurality of evaluation items, the relationships between the evaluation items and the rank values can be grasped more intuitively.

The cosmetic assist device of the present invention may further comprise an attribute estimation unit for estimating at least one of age and gender of the user from the face image of the user, wherein the similarity determination unit is configured to determine a subspace onto which the feature values are to be projected according an estimation result of the attribute estimation unit.

The evaluation items based on human impressions can be selected according to the age and gender estimated by the attribute estimation unit so that the similarly may be determined by using evaluation items that suit the user.

In the cosmetic assist device of the present invention, preferably, the prescribed feature values are represented by an N-dimensional vector, and the subspace consists of a subspace having a smaller number of dimensions than N.

The subspace having a smaller number of dimensions than N includes only the useful coordinate axes that are selected from the N-dimensional feature value space, and the determination capability (resolution power) on the selected evaluation items can be improved so that the accuracy in the determination of similarity can be improved.

The cosmetic assist device of the present invention may further comprise a make-up technique storage unit for storing a plurality of different cosmetic techniques, the make-up technique storage unit consisting of a rewritable database.

Thereby, the synthesized face images may be generated according to the cosmetic product information based on the current fashion trend and the season of the year.

The cosmetic assist device of the present invention may further comprise a synthesized face image storage unit for storing a plurality of synthesized face images generated by the synthesized face generation unit, the synthesized face generation unit being configured to generate a new synthesized face image when the contents of the make-up technique storage unit have been updated by applying the updated make-up technique to the base face image of the user, and to store the new synthesized face image in the synthesized face image storage unit.

Thereby, the synthesized face images may be generated according to the cosmetic product information based on the current fashion trend and the season of the year. Furthermore, when the user desires to compare the similarity of the synthesized face images to a different target face image, the existing synthesized face images can be reused in an advantageous manner.

The present invention also provides a cosmetic assist system, comprising: an image capturing unit for capturing a face image of a user; an input unit for inputting a target face image; a database for storing cosmetic techniques and image adjustment parameters corresponding to the individual cosmetic techniques; a synthesized face image generating unit for accessing the database to acquire the cosmetic techniques and the image adjustment parameters, and generating a plurality of synthesized face images obtained by applying the mutually different cosmetic techniques on the face image of the user by referencing the corresponding image adjustment parameters; a similarity determination unit for determining a degree of similarity between each synthesized face image and the target face image; and a cosmetic technique extraction unit for extracting one of the cosmetic techniques that was used to obtain the synthesized face image determined to have a highest degree of similarity by the similarity determination unit.

Thereby, a more appropriate cosmetic technique can be proposed according to the degree of similarity between the target face image and each synthesized face image obtained by applying a different cosmetic technique on the face image of the user.

The present invention also provides a cosmetic assist system, comprising: an information terminal incorporated with an image capturing unit for capturing a face image of a user and an input unit for inputting a target face image; and a server including a database for storing cosmetic techniques and image adjustment parameters corresponding to the individual cosmetic techniques, a synthesized face image generating unit for accessing the database to acquire the cosmetic techniques and the image adjustment parameters, and generating a plurality of synthesized face images obtained by applying the mutually different cosmetic techniques on the face image of the user by referencing the corresponding image adjustment parameters and a similarity determination unit for determining a degree of similarity between each synthesized face image and the target face image; wherein the information terminal is configured to transmit the face image of the user and the target face image to the server via a network, and acquire, from the server, one of the cosmetic techniques that was used to obtain the synthesized face image determined to have a highest degree of similarity by the similarity determination unit.

Thereby, the user is enabled to readily receive information on appropriate cosmetic techniques by accessing the server via an information terminal such as a smartphone and a tablet.

The present invention also provides a cosmetic assist system, comprising: an image capturing unit for capturing a face image of a user; an input unit for inputting a target face image; a database for storing cosmetic techniques and image adjustment parameters corresponding to the individual cosmetic techniques; a synthesized face image generating unit for accessing the database to acquire the cosmetic techniques and the image adjustment parameters, and generating a plurality of synthesized face images obtained by applying the mutually different cosmetic techniques on the face image of the user by referencing the corresponding image adjustment parameters; a similarity determination unit for determining a degree of similarity between each synthesized face image and the target face image; an evaluation unit for generating rank values for a prescribed evaluation item in regard to the face image of the user and the target face image; and a display unit for displaying one of the cosmetic techniques that was used to obtain the synthesized face image determined to have a highest degree of similarity by the similarity determination unit and the rank values.

Thereby, according to the degree of similarity between the target face image and each synthesized face image obtained by applying a different cosmetic technique on the face image of the user, a make-up technique that can make the user's face look similar to the target face image can be proposed, and the difference between the user's face and the target face image can be displayed as a numerical value on each evaluation item based on human impressions.

The present invention also provides a cosmetic assist system, comprising: an information terminal incorporated with an image capturing unit for capturing a face image of a user and an input unit for inputting a target face image; and a server including a database for storing cosmetic techniques and image adjustment parameters corresponding to the individual cosmetic techniques, a synthesized face image generating unit for accessing the database to acquire the cosmetic techniques and the image adjustment parameters, and generating a plurality of synthesized face images obtained by applying the mutually different cosmetic techniques on the face image of the user by referencing the corresponding image adjustment parameters, a similarity determination unit for determining a degree of similarity between each synthesized face image and the target face image and an evaluation unit for generating rank values for a prescribed evaluation item in regard to the face image of the user and the target face image; wherein the information terminal is configured to transmit the face image of the user and the target face image to the server via a network, and acquire, from the server, and display one of the cosmetic techniques that was used to obtain the synthesized face image determined to have a highest degree of similarity by the similarity determination unit and the rank values.

Thereby, the user is enabled to readily receive information on appropriate cosmetic techniques and the rank values by accessing the server via an information terminal such as a smartphone and a tablet and display the such data on the information terminal.

The present invention also provides a cosmetic assist method, comprising the steps of: capturing a face image of a user; inputting a target face image; generating a plurality of synthesized face images obtained by applying mutually different cosmetic techniques on the face image of the user; determining a degree of similarity between each synthesized face image and the target face image; and extracting one of the cosmetic techniques that was used to obtain the synthesized face image determined to have a highest degree of similarity.

Thereby, a more appropriate cosmetic technique can be proposed according to the degree of similarity between the target face image and each synthesized face image obtained by applying a different cosmetic technique on the face image of the user.

The present invention also provides a cosmetic assist method, comprising the steps of: capturing a face image of a user; inputting a target face image; generating a plurality of synthesized face images obtained by applying mutually different cosmetic techniques on the face image of the user; determining a degree of similarity between each synthesized face image and the target face image; generating rank values for a prescribed evaluation item in regard to the face image of the user and the target face image; and displaying one of the cosmetic techniques that was used to obtain the synthesized face image determined to have a highest degree of similarity and the rank values.

Thereby, according to the degree of similarity between the target face image and each synthesized face image obtained by applying a different cosmetic technique on the face image of the user, a make-up technique that can make the user's face look similar to the target face image can be proposed, and the difference between the user's face and the target face image can be displayed as a numerical value on each evaluation item based on human impressions.

The present invention also provides a cosmetic assist computer program for: inputting a face image of a user and a target face image; generating a plurality of synthesized face images obtained by applying mutually different cosmetic techniques on the face image of the user; determining a degree of similarity between each synthesized face image and the target face image; and extracting one of the cosmetic techniques that was used to obtain the synthesized face image determined to have a highest degree of similarity.

Thus, by using a dedicated machine, a terminal of a client-server system, a smartphone or a tablet, incorporated with the cosmetic assist computer program, a more appropriate cosmetic technique can be proposed according to the degree of similarity between the target face image and each synthesized face image obtained by applying a different cosmetic technique on the face image of the user.

The present invention also provides a cosmetic assist computer program for: inputting a face image of a user and a target face image; generating a plurality of synthesized face images obtained by applying mutually different cosmetic techniques on the face image of the user; determining a degree of similarity between each synthesized face image and the target face image; generating rank values for a prescribed evaluation item in regard to the face image of the user and the target face image; and displaying one of the cosmetic techniques that was used to obtain the synthesized face image determined to have a highest degree of similarity and the rank values.

Thus, by using a dedicated machine, a terminal of a client-server system, a smartphone or a tablet, incorporated with the cosmetic assist computer program, a more appropriate cosmetic technique can be proposed according to the degree of similarity between the target face image and each synthesized face image obtained by applying a different cosmetic technique on the face image of the user, and the difference between the user's face and the target face image can be displayed as a numerical value on each evaluation item based on human impressions.

According to the present invention, a more appropriate cosmetic technique can be proposed according to the degree of similarity between the target face image and each synthesized face image obtained by applying a different cosmetic technique on the face image of the user, and the difference between the user's face and the target face image can be displayed as a numerical value on each evaluation item based on human impressions.

BRIEF DESCRIPTION OF THE DRAWINGS

FIG. 8 is a table listing the contents (sensuous attributes) of the evaluation items based on human impressions;

FIG. 14 is a block diagram showing the structure of the cosmetic assist device of a fourth embodiment of the present invention.

DESCRIPTION OF THE PREFERRED EMBODIMENT(S)

First Embodiment

Figure 1:
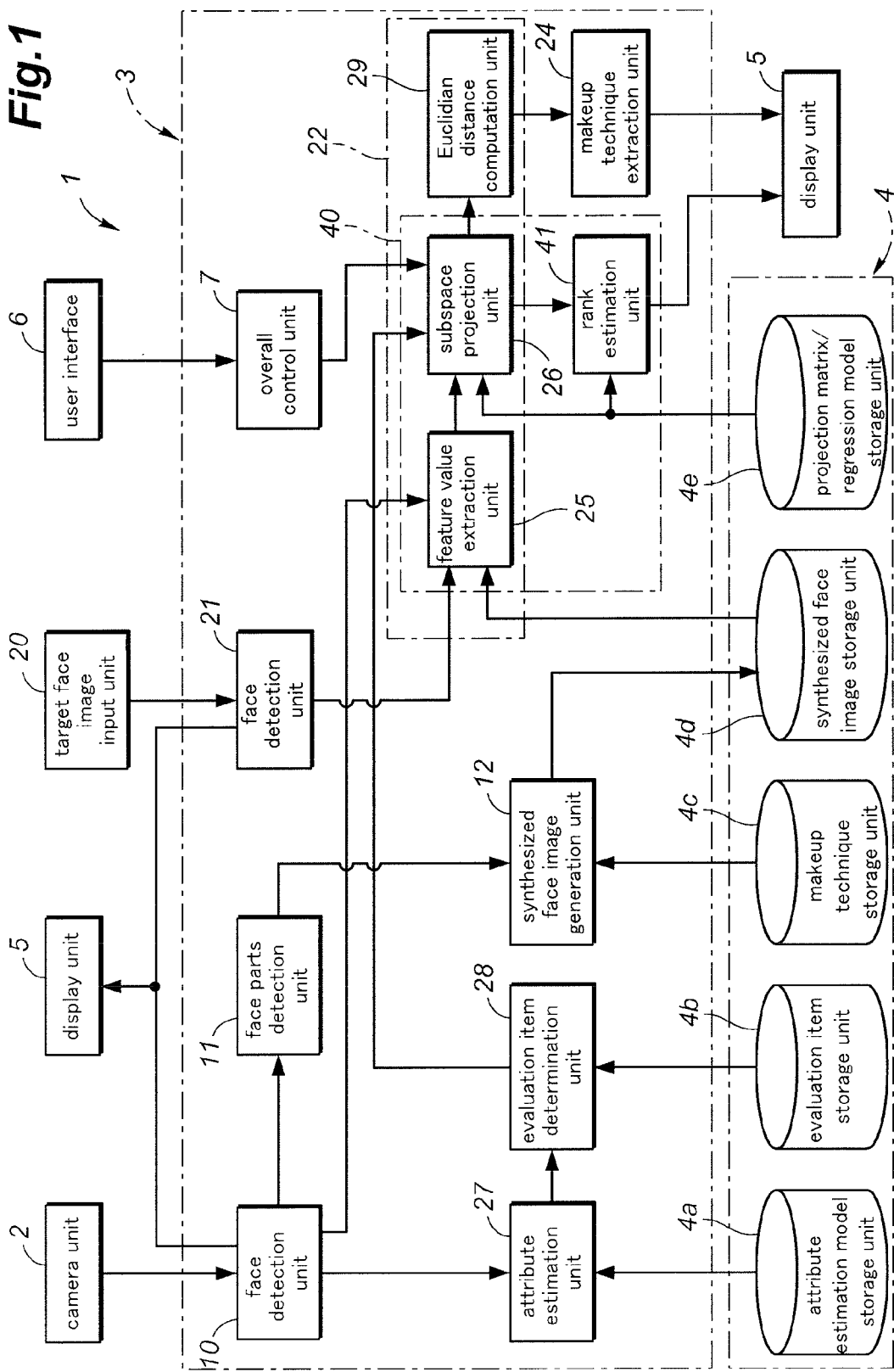
FIG. 1 is a block diagram showing the structure of a cosmetic assist device given as a first embodiment of the present invention.

FIG. 1 is a block diagram showing a cosmetic assist device 1 given as a first embodiment of the present invention. The structure and functionality of the cosmetic assist device 1 of the first embodiment are described in the following. In the illustrated embodiment, a user who is about to apply a facial make-up operation to herself uses the device of the present invention on her own. However, similar structures may be implemented for other cosmetic operations.

A shown in FIG. 1, the cosmetic assist device 1 comprises a camera unit (image capturing unit) 2, a target face image input unit (input unit) 20, an image processing unit 3, a storage unit 4, a display unit 5 and a user interface 6.

The camera unit 2 may be provided with an imaging device such as CCD (charge coupled device) and CMOS (complementary metal oxide semiconductor), and produces image data based on the captured image at the rate of 15 fps (frames per second), for instance. An image processing circuit (not shown in the drawings) incorporated in the camera unit 2, for instance, performs per se known image processing techniques such as demosaicing, color correction, white balance correction and gamma correction to the image data obtained by the camera unit 2.

Then, the image processing unit 3 performs various processes on the preliminarily processed image data by referencing the data stored in the storage unit 4. The image data that is subjected to the image processes may be temporarily stored in memory not shown in the drawings to activate subsequent components, after being processed by the various components of the image processing unit 3. The hardware and software may be configured such that the various components may operate in a pipeline mode.

FIG. 1 contains two display units 5, but this is purely for the convenience of illustration, and may be combined into a single unit.

The storage unit 4 includes an attribute estimation model storage unit 4a, an evaluation item storage unit 4b, a make-up technique storage unit 4c, a synthesized face image storage unit 4d and a projection matrix/regression model storage unit 4e as databases. The projection matrix and the regression model stored in the projection matrix/regression model storage unit 4e are two distinct sets of data.

The make-up technique storage unit 4c and the synthesized face image storage unit 4d are different from other databases in being rewritable. Other storage units are read only databases that store prefixed data therein. As will be discussed hereinafter, the synthesized face image is generated by a synthesized face image generation unit 12 referencing the data stored in the make-up technique storage unit 4c, and the generated synthesized face image is stored in the synthesized face image storage unit 4d. Depending on the mode of generating the synthesized face image, the amount of data required for the synthesized face image of the user may become significantly great.

As will be discussed hereinafter, the degree of similarity between the synthesized face image and the target face image is determined, and once the optimum make-up technique has been obtained, the synthesized face image may be deleted, but it is also possible to reuse the generated synthesized face image at a later time. More specifically, a same user may desire to determine the degree of similarity to another target face image, by storing the generated synthesized face images for later use, the need for generating the same synthesized face image may be eliminated.

For this reason, it is desirable to have the data capacity of the synthesized face image storage unit 4d to be greater than those of other databases. Therefore, the synthesized face image storage unit 4d preferably consists of a mass storage unit such as a hard disk drive. If the data of a plurality of users is to be handled, a RAID (redundant array of inexpensive disks) may be formed by a plurality of hard disk drives so that a high reliability can be achieved, and the data transfer speed can be increased.

In the following description, the synthesized face images are stored in the synthesized face image storage unit 4d as image data. However, it is also possible to store in the synthesized face image storage unit 4d feature values which are extracted by a feature value extraction unit 25 as will be discussed hereinafter.

The structure of the image processing unit 3 is described in the following. First of all, the functionality of the image processing unit 3 of the cosmetic assist device 1 is briefly described in the following. The synthesized face image generation unit 12 applies various make-up techniques (or performs various simulations) on the face image of the user contained in the image captured by the camera unit 1, and thereby generates face images (synthesized face images). The similarity determination unit 22 determines the degree of similarity between each synthesized face image and the target face image, and extracts the particular make-up technique that was applied to produce the synthesized face image having the highest degree of similarity to the target face image. This make-up technique is displayed on the display unit 5. This is now described in the following in greater detail.

The face detection unit 10 detects a face image from the image captured by the camera unit 2, and if a face image is contained therein, the face image is cut out, and is forwarded to a face parts detection unit 11. The face parts detection unit 11 detects face parts such as eyes, a nose and a mouth.

The face image cut out by the face detection unit 10 is also forwarded to an attribute estimation unit 27. The attribute estimation unit 27 estimates attributes such as age, gender and race from the face image according to an attribute estimation models stored in an attribute estimation model storage unit 4a. The estimation result is forwarded to an evaluation item determination unit 28. Based on the estimation result, the evaluation item determination unit 28 determines the evaluation items that are to be used for determining the degree of similarity from "the various evaluation items based on human impressions". In the following description, the term "the various evaluation items based on human impressions" is simply referred to as "evaluation items based on human impressions" and "evaluation items".

The target face input image unit 20 is used for inputting the target face image which the user desires to achieve prior to actually applying the make-up to the user. This target face image may be obtained by capturing the face image of a third party by using a digital camera and storing the face image in a portable image storage medium or may be obtained by searching the face image of an actress on the Internet. Alternatively, the face image may be captured directly by the camera unit 2. In the cosmetic assist device 1 of the first embodiment, to permit a wide range of sources for the face image, the image fed to the target face image input unit 20 may include extraneous parts that do not contribute to the determination of the degree of similarly and should be removed from the beginning. The image obtained by the target face image input unit 20 is forwarded to the face detection unit 21 to be extracted only of the face part thereof. The face detection unit 21 and the face detection unit 10 are given as two separate units, but may also be formed as a single combined unit.

The structure of the similarity determination unit 22 is described in the following. The similarity determination unit 22 comprises a feature value extraction unit 25, a subspace projection unit 26 and a Euclidian distance computation unit 29. Each of the synthesized face images stored in the synthesized face image storage unit 4d and the target face image cut out by the face detection unit 21 are forwarded to the feature value extraction unit 25 of the similarity determination unit 22.

The feature value extraction unit 25 extracts localized feature values such as Gabor features or LBPs (local binary patterns) from the received synthesized face image. The feature value extraction unit 25 extracts localized feature values also from the target face image. The feature values thus obtained typically consist of a multi-dimensional (N-dimensional) vectors.

The feature values extracted by the feature value extraction unit 25 are projected onto a prescribed subspace in the subspace projection unit 26. This subspace is a vector space of a smaller number of dimensions than the N-dimensional vector formed by the feature values, and, in the illustrated embodiment, directly corresponds to an evaluation item based on human impressions such as those mentioned above. By using this subspace, the degree of similarity between each synthesized face image and the target face image in the subspace and the rank values (scores) of the synthesized face images can be individually obtained. The procedure for generating the subspace is described hereinafter.

The subspace projection unit 26 projects the feature values of the synthesized face images and the target face image onto the subspace corresponding to the evaluation items determined by the evaluation item determination unit 28 according to the gender, age and so on estimated by the attribute estimation unit 27. Thereby, the coordinate values of the synthesized face images and the target face image in the subspace are determined. The projection is an operation that generates a vector of a smaller number of dimensions than the N-dimensional vector formed by the feature values. For instance, when the number of dimensions following the projection is N1, this operation corresponds to the multiplication of an N1×N matrix to an N-dimensional vector.

The Euclidian distance computation unit 29 computes the distance between two coordinates according to the coordinate values of each synthesized face image and the target face image which are projected onto the subspace. The make-up technique extraction unit 24 then selects the technique that achieves a synthesized face image which is closest to the target face image of all the make-up techniques according to the output of the Euclidian distance computation unit 29, and displays the obtained result on the display unit 5.

The structure of an evaluation unit 40 is described in the following. The evaluation unit 40 is formed by a rank estimation unit 41 as well as the feature value extraction unit. 25 and the subspace projection unit 26. The feature value extraction unit 25 and the subspace projection unit 26 are not described here because they were already discussed earlier. The rank estimation unit 41 accesses the projection matrix/regression model storage unit 4e, and acquires the rank value of each evaluation item by using an evaluation item regression model according to the feature values of the synthesized face image or the target face image. The acquired rank values are displayed on the display unit 5.

The overall control unit 7 is described in the following. The cosmetic assist device 1 includes, as the hardware for controlling the operation of each of the structural components discussed above, a CPU (central processing unit) or a MPU (micro processing unit) serving as a computing unit not shown in the drawings, ASICs (application specific integrated circuits), work memory, program memory and a parallel/serial bus for allowing exchange of data between the various structural components in a per se known arrangement.

The functional blocks shown in FIG. 1 are not required to be entirely made of hardware, but may be implemented by the computing unit mentioned above and associated software. All of these structural components may be implemented in a laptop computer with a camera, a smart phone or a tablet computer.

The cosmetic assist device 1 is provided with a user interface 6. The user interface 6 may consist of a common input device such as a keyboard, a mouse and a touch panel, and the user is enabled to feed commands to the cosmetic assist device 1 via the overall control unit 7 by operating the user interface 6. As an example, the user may command the selection of images on the target face image input unit 20.

Figure 2:
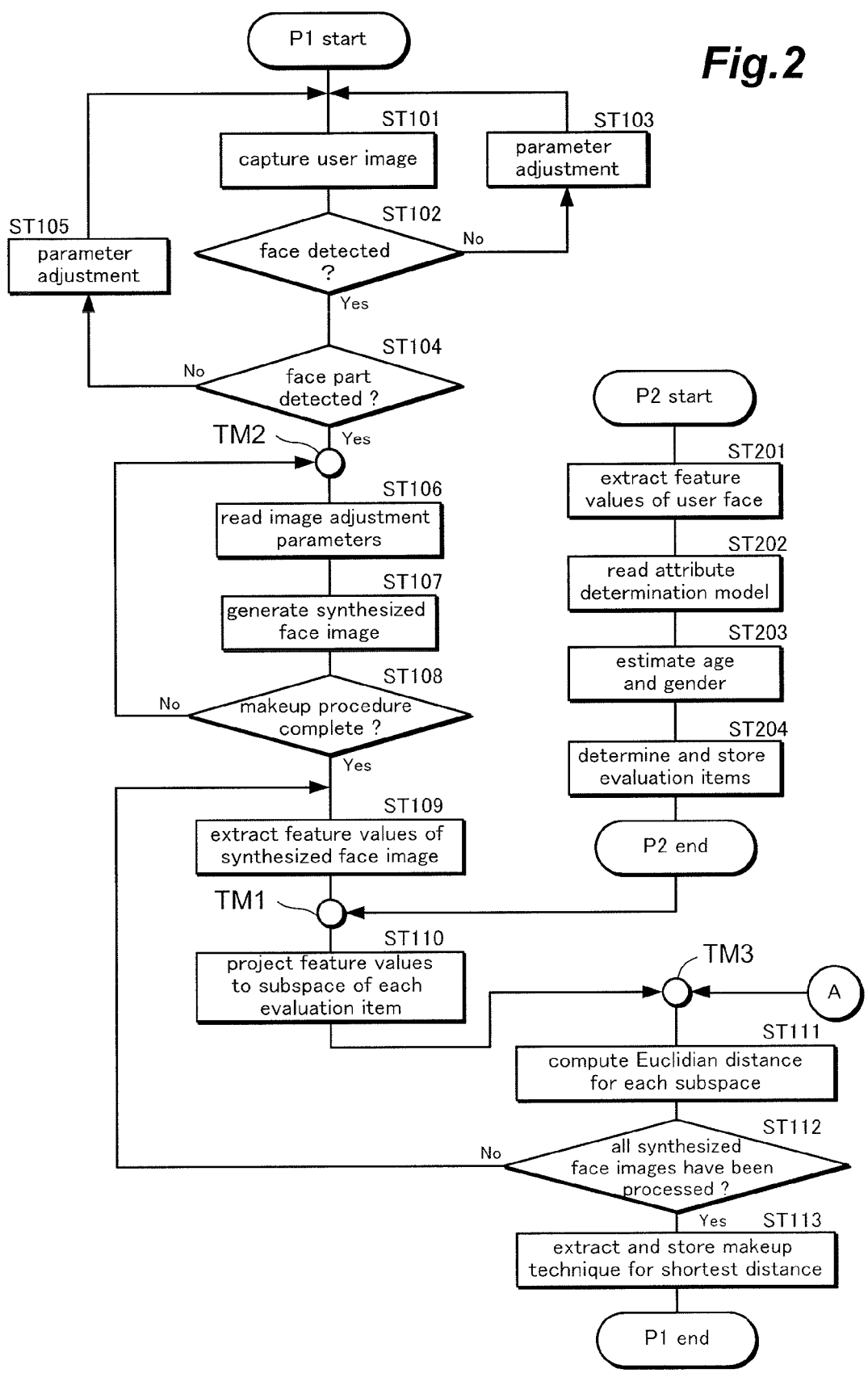
FIG. 2 is a flowchart showing the process of determining similarity in the cosmetic assist device of the first embodiment.
Figure 3:
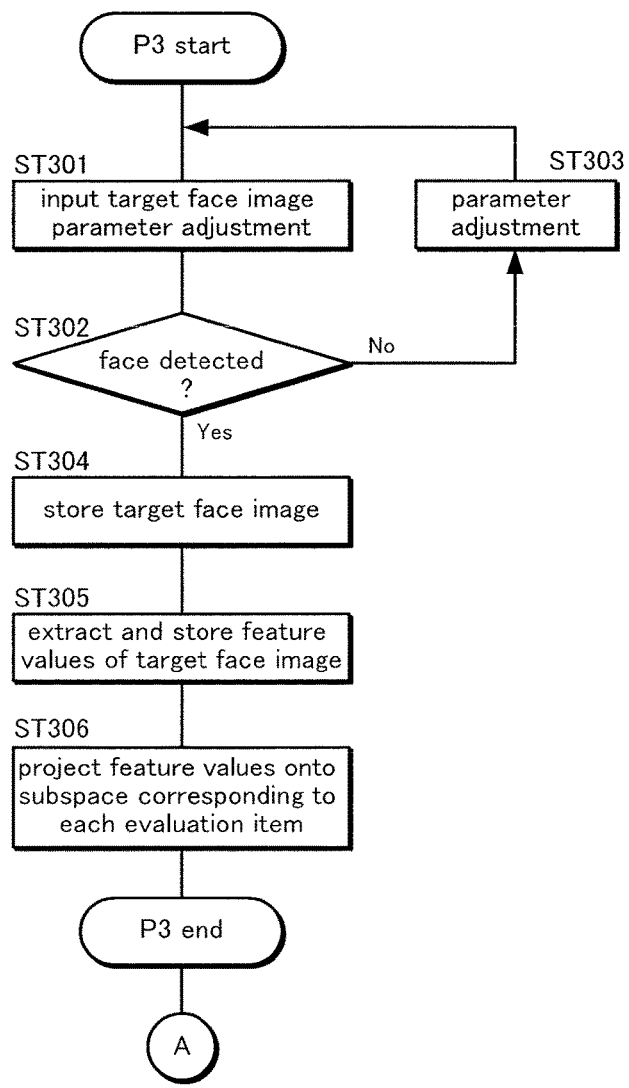
FIG. 3 is a flowchart showing the process of determining similarity in the cosmetic assist device of the first embodiment.

FIGS. 2 and 3 are flowcharts for illustrating the process of determining the degree of similarity in the cosmetic assist device 1 of the first embodiment. In the following, the mode of operation of the cosmetic assist device 1 of the first embodiment and the image processing algorithm used in the cosmetic assist device 1 are described with reference to FIGS. 2 and 3 in addition to FIG. 1. In the following description, reference is made to a new drawing every time an important point is discussed.

The flowcharts shown in FIGS. 2 and 3 contain three program modules P1, P2 and P3, and TM1, TM2 and TM3 in the flowcharts indicate the points of synchronization. More specifically, program P2 is required to be executed at least before the program flow of program P1 has advanced to TM1, and program P3 is required to be executed at least before the program flow of program P1 has advanced to TM3 for the first time. Program P3 is connected to program P1 at connecting point A.

First of all, the process in program P1 is described in the following. The camera unit 10 captures an image containing the face of the user (step ST101). The image may be captured from a motion picture by using the user interface 6 or may be captured as a still picture from the beginning.

The obtained image data is subjected to a preliminary process as discussed earlier, and is used for detecting a face by the face detection unit 10. It is then determined if a face has been successfully detected (step ST102).

As a common procedure for detecting a face, a pattern recognition technique based on a statistical learning process may be used. According to this technology, the parameters for an identifier are determined from samples for learning. The identifier may be based on a neural network, a support vector machine or a Bayesian inference machine. These techniques consist of a feature selection technique for extracting feature values for identification purpose from the input image, an identifier construction technique for constructing an identifier for identifying an object using the extracted features values as an input and a technique for determining if a face is found within a window by using the constructed identifier.

The technique for determining if a face is found may consist of a process based on four directional features and a linear discriminant analysis, for instance. According to this technique, an input image is scan searched from a search area determined from the skin color information and motion information in the captured image via a template using four directional features, and a region identified as a pattern of a face and a head is detected by using a linear discriminant analysis.

The four directional features are feature values which are engineered to simulate a visual cortex, and have the advantages of being robust against the geometrical changes in the edges and requiring a small amount of computation. The four directional features assign the edge gradient of each pixel to four directional planes, and are known as a simplified version of Gabor features.

The linear discriminant analysis consists of a technique for finding a projection matrix for two or more clusters (given as the object of determination) that minimizes the within-class variance and maximizes the between-class variance. The received feature values are projected onto a determination space by using a mapping matrix obtained by the linear discriminant analysis, and the identification result is obtained as the class that minimizes the distance to the average vector of the determination class. Generally in such face recognition techniques, as the reliability of each identification process can be computed, it can be determined if a face has been successfully detected or not by comparing the obtained reliability value with a prescribed threshold valve.

If a face has been successfully detected (yes in step ST102), the program flow advances to step ST104. If not (no in step ST102), the parameters of the camera unit 2 such as charge accumulation time and the frame rate, and the threshold value for face detection are adjusted (in step ST103), and the face image of the user is captured once again (step ST101). If no renewed image capturing is required (such as when the adjustment of the image can be accomplished by the adjustment of the contrast or gamma value), the capturing of the face image may be finalized by the preliminary processing so that the face detection may be performed only with some correction of the image. Also, by producing a code for identifying the cause of the failure of face detection, along with the degree of reliability, the parameters may be adjusted by referencing such data so that the image suitable for face detection may be obtained with a minimum number of tries.

Even when a face detection has been successfully accomplished in step ST102, the size of the face frame containing the face and the direction and position of the face in the face frame may vary to such an extent that the degree of similarity with respect to another face image cannot be accurately evaluated. More specifically, the image must be normalized so that the face is fitted into a prescribed face frame. A number of techniques are known as such a technique, such as the technique to detect eyes in the detected face frame and to normalize the image by performing an affine transformation on the face image according to the position of the eyes, and the technique to apply an AAM (active shape model) to the detected face frame and to normalize the image by performing an affine transformation on the face frame. By performing any of such techniques, the size of the detected face frame is unified (such as 100 by 100 pixels), and the face frame is normalized so that the face is placed in the center of the face frame.

Following the detection of a face from the image captured by the camera unit 2, the face parts detection unit 11 detects the position of face parts such as eyes, a nose and a mouth, and it is determined if the face parts detection has been successfully performed (step ST104). The face parts detection unit 11 is configured to detect the face parts such as eyes, a nose and a mouth by using the four directional features and the relaxation matching.

Another technique that can be used in the first embodiment is to detect the face and each face part by using Haar-like features. The nose which is the easiest to detect of all the face parts is used as a reference for estimating the candidate region for each face part according to the relative positional relationship. At this time, a template matching using HOG (histogram of oriented gradient) feature values may be performed in the region adjoining each candidate region to finely adjust the position of each face part. The HOG feature values are obtained from a histogram of gradient directions of luminance in prescribed localized regions (cells), and the template matching based on HOG feature values are said to allow the feature values to be extracted with relative ease even when geometrical transformations are performed, and to be robust against changes in the intensity of illumination.

As the reliability of detection can be computed in the determination of face parts also, it can be determined if the face part detection has been successfully performed by comparing the reliability with a prescribed threshold value. If the face part detection has been successful (yes in step ST104), the program flow advances to step ST106. If not (no in step ST104), parameters for image capturing are adjusted (step ST105), and the image of the user is captured once again (step ST101). The process in step ST105 is omitted from the disclosure as it is similar to that in step ST103.

The synthesized face image generation unit 12 then accesses the make-up technique storage unit 4c, and reads out image adjustment parameters (step ST106) before a synthesized face image is generated (step ST107).

Figure 4:
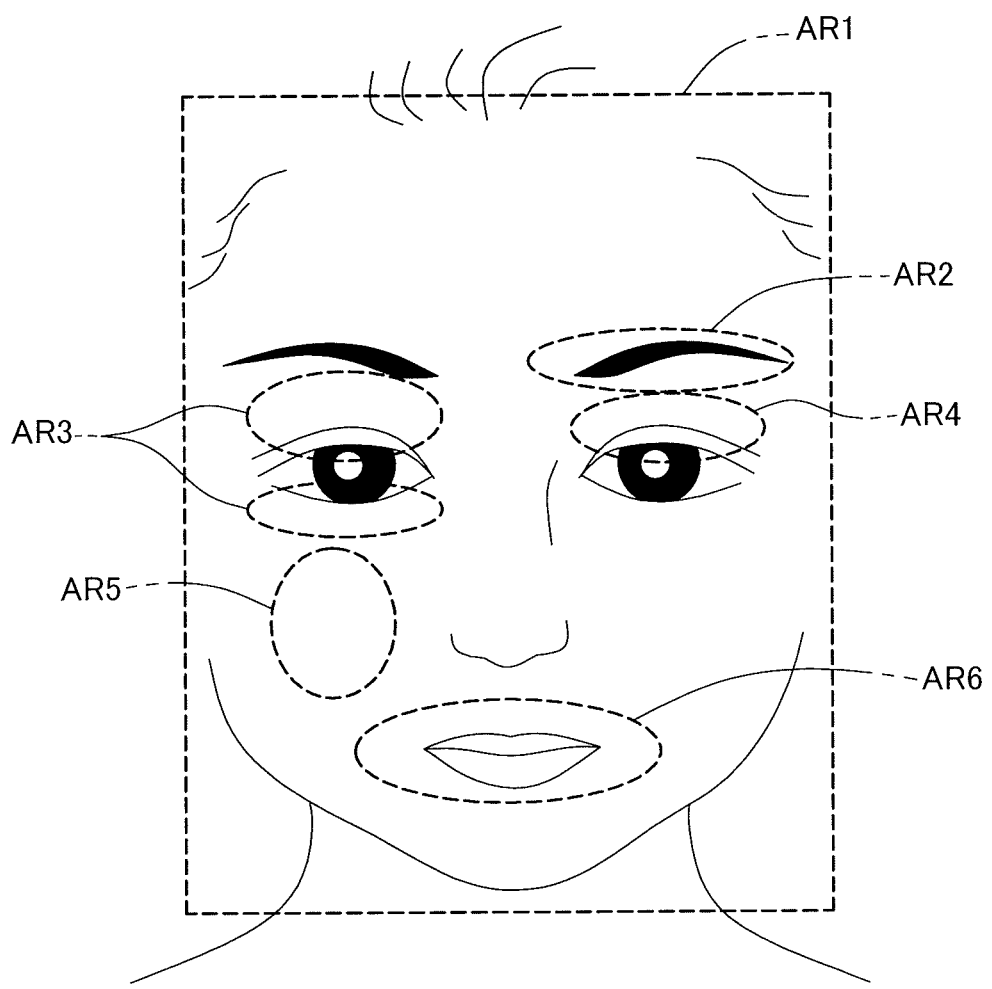
FIG. 4 is a diagram illustrating the object of image processing in generating a synthesized face image.

FIG. 4 is a diagram illustrating the object of image processing when generating a synthesized face image. The object of image processing and the contents of the parameters for image adjustment for image synthesis are described in the following with reference to FIG. 4 in combination with FIG. 1.

In FIG. 4, AR1 to AR6 denote various regions (areas) to each of which a cosmetic operation is to be performed. More specifically, AR1 denotes the entire face, AR2 denotes an area where eye shadow is to be applied, AR3 denotes the area where an eyebrow is to be drawn, AR4 denotes the area where an eye line is to be drawn, AR5 denotes the area where cheek shadow or color is to be applied and AR6 denotes the area where a lipstick is to be applied. AR2 to AR5 occur on either side of the face, but regions on one side of the face are omitted in the following description.

The synthesized face image is generated as a simulation of applying cosmetic operation on each of such areas, and the contents of the cosmetic operations are defined for either a simple mode or a detailed mode in the first embodiment.

In the simple mode, one of two cosmetic products (foundations) of different colors (FAC1 and FAC2) is applied to AR1. One of three cosmetic products of different colors (EBC1 to EBC3) is applied to AR2. One of three cosmetic products of different colors (ESC1 to ESC3) is applied to AR3. One of two cosmetic products of different colors (ELC1 and ELC2) is applied to AR4. One of four cosmetic products of different colors (CEC1 and CEC4) is applied to AR5. One of four cosmetic products of different colors (LPC1 and LPC4) is applied to AR6. Thus, cosmetic techniques combining these cosmetic products may have 576 (2×3×3×2×4×4=576) different combinations. In the following description, the letters such as FAC1 and LPC1 indicating different colors are referred to simply as "color symbol".

In the detailed mode, one of six cosmetic products of different colors (FAC1 to FAC6) is applied to AR1. One of three cosmetic products of different colors (EBC1 to EBC3) is applied to AR2, and an eyebrow which is either fine, normal or bold is applied to AR2. One of 18 cosmetic products of different colors (ESC1 to ESC18) is applied to AR3, and an eye shadow which is either fine, normal or bold is applied to AR3. One of two cosmetic products of different colors (ELC1 and ELC2) is applied to AR4. One of four cosmetic products of different colors (CEC1 and CEC4) is applied to any one of three possible areas (upper cheek, lower cheek and entire cheek) in AR5. One of eight cosmetic products of different colors (LPC1 to LPC8) is applied to AR6. Thus, cosmetic techniques combining these products may have 559,872 (6×(3×)×(18×3)×2×(4×3)×8=559,872) different combinations.

The make-up technique storage unit 4c stores, as the image adjustment parameters corresponding to each make-up technique, color symbols, specific names of the cosmetic products corresponding to the color symbols, information (color change information) on the changes in the color of the skin (luminance, saturation and hue) that are caused by the application of these cosmetic products, shape information on the eyebrows drawn in AR2 (image data corresponding to being fine, standard and bold) and the procedures of cosmetic operations.

The color change information may include a color adjustment factor that adjusts the effect of the cosmetic operation in the simulation depending on the luminance, saturation and hue of the face image of the user captured by the camera unit 2. The color adjustment factor may consist of a correction ratio in a L*a*b* color space, and this takes into account the fact that the effect of applying a foundation having a certain color to a person having a similar skin color is very slight. Because a cosmetic operation consists of applying powder or liquid onto the skin of the user, it is possible to improve the precision in predicting the changes in the luminance, saturation and hue of the user as a result of the cosmetic operation by making use of a layer model which is used in the field of electrophotography to determine the effect of the deposition of a powder toner or liquid ink containing certain pigments or dies on a recording medium having a certain color (skin color).

The shape information may contain a scaling adjustment factor which accounts for the size of each face part. This adjustment factor may be used for adjusting the horizontal dimension and inclination of an eye line or an eyebrow according to the size of the eye obtained from the detected face image.

Figure 5:
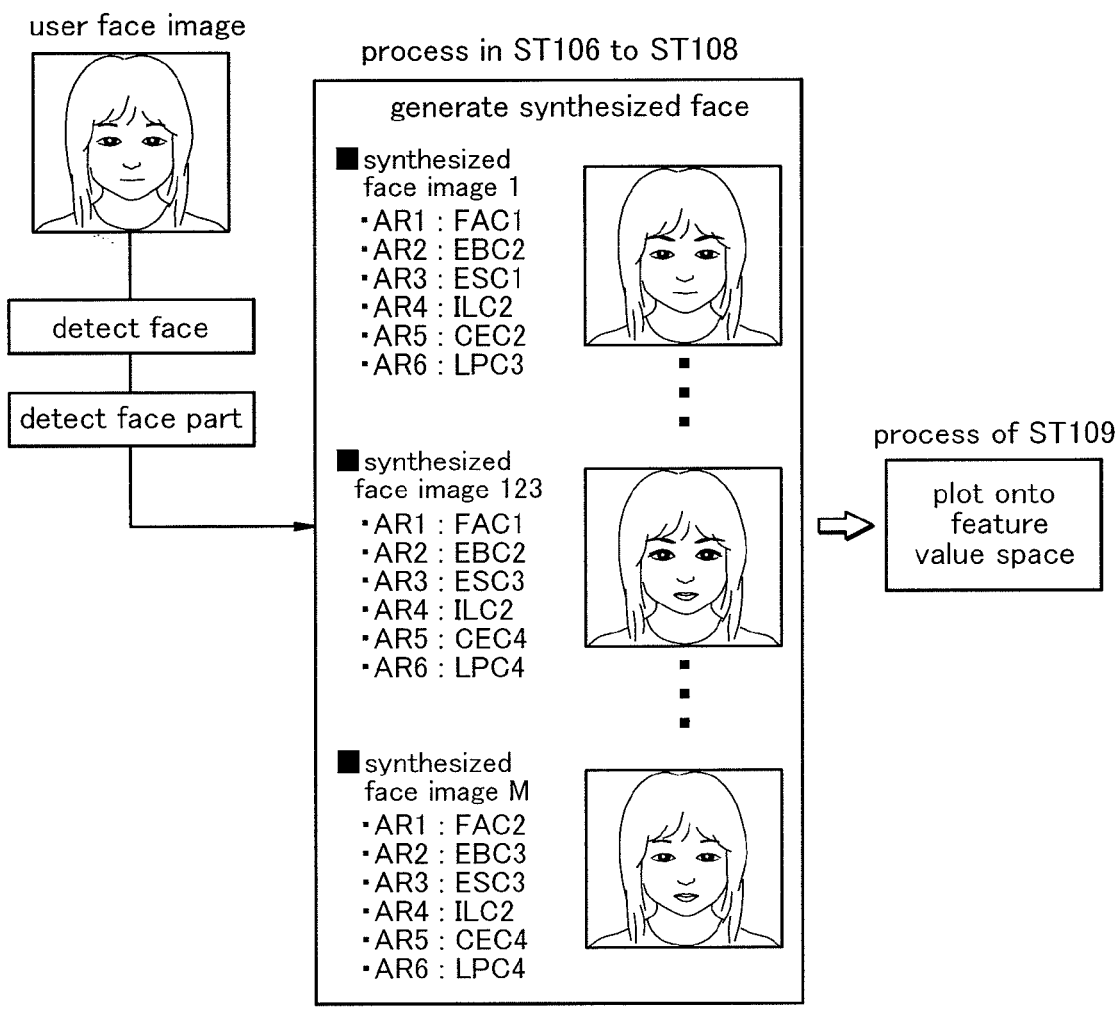
FIG. 5 is a diagram illustrating the process of generating the synthesized face image in the cosmetic assist device of the first embodiment.

FIG. 5 is a diagram illustrating the process of generating a synthesized face image in the cosmetic assist device 1 of the first embodiment. Reference is made to FIGS. 1, 2 and 5 in the following description. The synthesized face image generation unit 12 acquires the various color adjustment parameters such as the color information, the shape information, the color adjustment factor, the scaling adjustment factor and the procedures of cosmetic operations from the make-up technique storage unit 4c storing a database, and by referencing the position of each face part detected by the face parts detection unit 11, a synthesized face image is generated from the face image of the particular user and the image adjustment parameters. This process is repeated for each of the entire combinations of AR1 to AR6 in 576 different ways in the simple mode and in 559,872 different ways in the detailed mode (yes in step ST108). The generated synthesized face images are stored in the synthesized face image storage unit 4d.

More specifically, as shown in FIG. 1, for instance, a synthesized face image 1 is created by applying FAC1 to AR1, EBC2 to AR2, ESC1 to AR3, ELC2 to AR4, CEC2 to AR5 and LPC3 to AR6. This is repeated until all such combinations are applied to AR1 to AR6, and synthesized face images 1 to M (M=576 in the case of the simple mode).

The "make-up technique" as used in this description means the individual combination of make-up operations that are applied to the face image of the user to create each synthesized face image. In other words, each synthesized face image corresponds to a different make-up technique.

Figure 6:
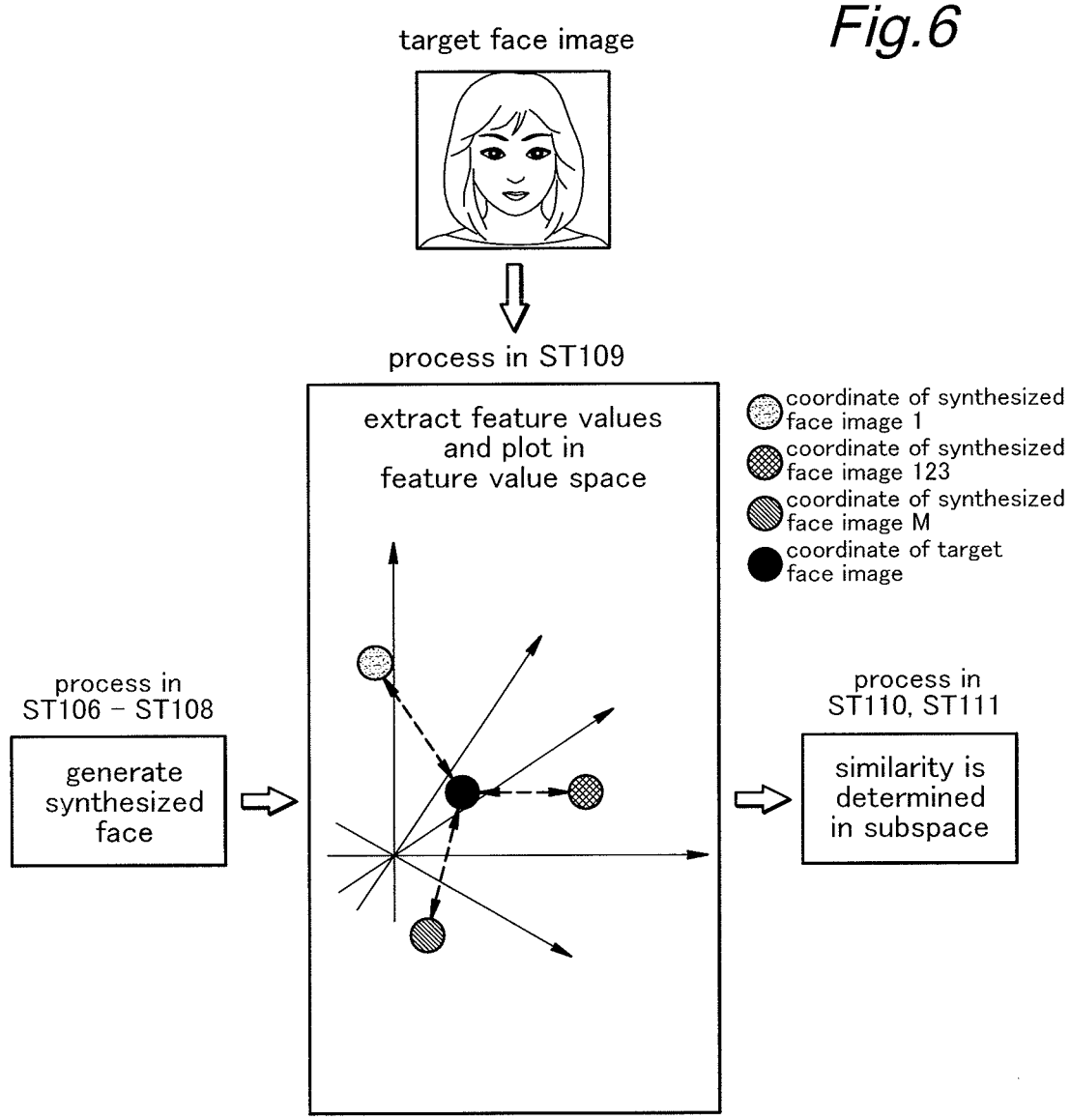
FIG. 6 is a diagram illustrating the process of plotting the feature values in the feature value space in the cosmetic assist device of the first embodiment of the present invention.

FIG. 6 is a diagram illustrating the process of plotting the feature values in a feature value space in the cosmetic assist device 1 of the first embodiment.

Reference is made to FIGS. 1, 2 and 6 in the following description. The feature value extraction unit 25 retrieves the synthesized face images of the user that are stored in the synthesized face image storage unit 4d, and the feature values extracted therefrom are plotted in the feature value space (step ST109).

The first embodiment uses Gabor feature values or the LBP (local binary pattern) as the features values. Each Gabor feature value is extracted by a Gabor filter which is obtained by localizing a sin/cos function with a Gaussian function. In other words, an edge and the luminance (intensity) of the edge can be extracted by convoluting the image data with the Gabor filter. The feature values obtained in this manner are said to be robust against variations in the illumination as they are obtained by extracting localized features.

The LBP feature values consist of bit trains obtained by comparing the luminance of a pixel of interest with those of the surrounding eight pixels. Based on these feature values, an edge in the localized region can be extracted. The LBP method is known to be robust against variations in the illumination and require little computational cost. As the LBP values consist of bit trains or numerical values, one may extract the LBP values from a given image, and use a histogram based on the ranks or the frequencies of the values as the feature values. More specifically, a synthesized face image is divided into a plurality of blocks, and a histogram of LBP feature values is created for each of the blocks. A vector that is created by connecting these histograms may be used as a final LBP feature vector.

The Gabor feature values and the LBP feature values allow a change in density owing to the creation of an edge (eye shadow, eye line and cheek shadow or color) to be extracted. In particular, the Gabor feature values allow a change to be extracted even when an existing edge is emphasized (eye line and lipstick) and the overall luminance of the face is changed by the application of a foundation.

By means of these operations, the luminance vector of each face image is converted into a feature value vector and plotted in the feature value space shown in FIG. 6. However, the feature value space represents the overall appearance via the feature values, and may be considered as an "appearance space". Therefore, when the two sets of coordinates plotted by the feature values extracted from two different face images are close to each other, it means that the two face images look similar in appearance.

In the first embodiment, each synthesized face image is normalized as a 100 by 100 pixel image as discussed earlier, and the Gabor feature values and the LBP feature values are obtained from these normalized face images.

Figure 7:
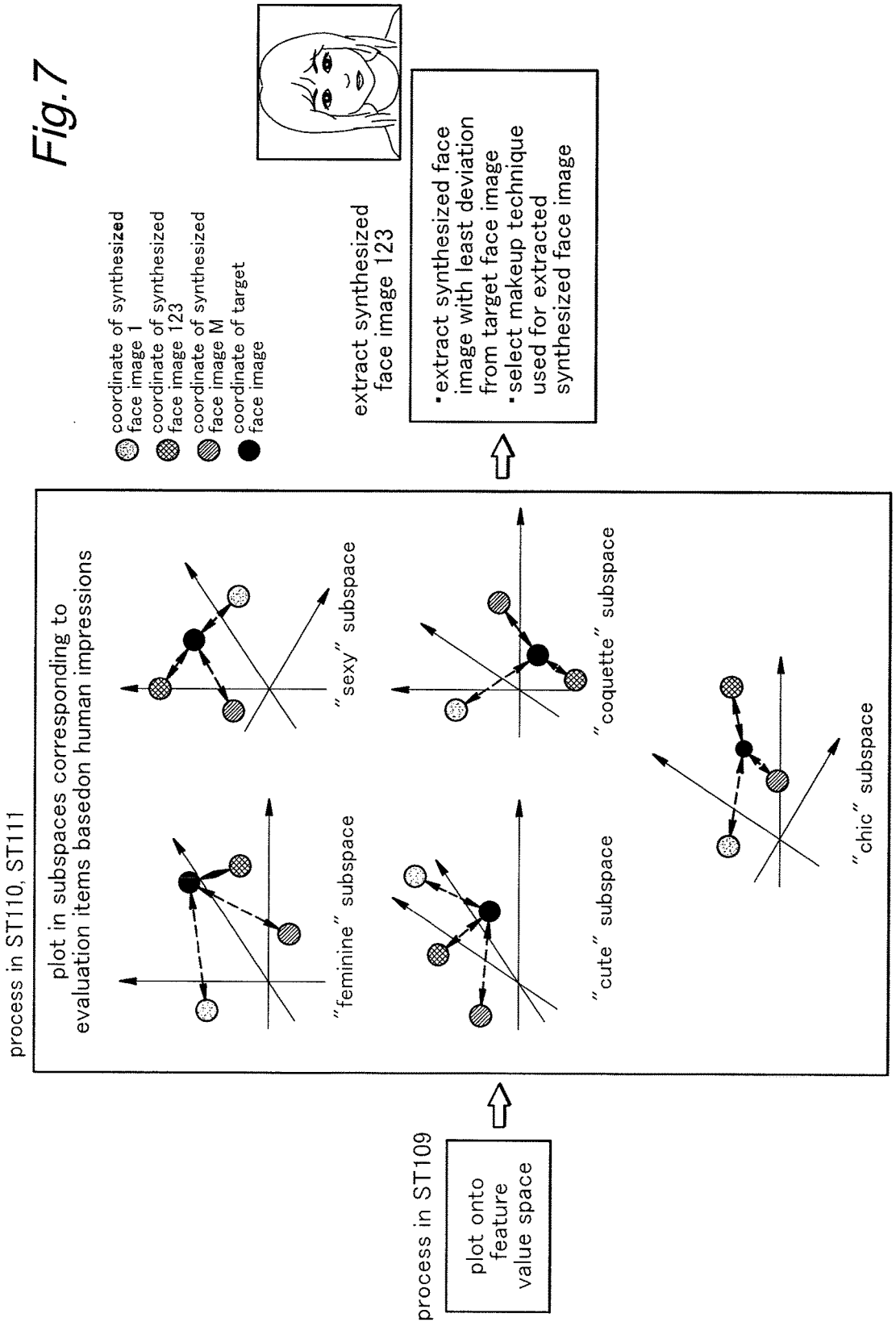
FIG. 7 is a diagram illustrating the process of projecting the feature values onto a subspace in the cosmetic assist device of the first embodiment of the present invention.

FIG. 7 is a diagram showing the process of projecting the feature values onto subspaces in the cosmetic assist device 1 of the first embodiment. FIG. 8 shows a table listing the contents (sensuous properties) of the evaluation items based on human impressions.

Reference is made to FIGS. 2, 7 and 8 in the following description. In step ST110, each of the feature value vectors discussed above is projected onto a subspace representing the evaluation item based on human impressions in step ST110.

In the first embodiment, as shown in FIG. 8, for females of age 20 or less, "feminine", "cute" and "child-like" are selected as the evaluation items. For females of age 20 to 30, five items, "feminine", "cute", "chic", "coquette" and "sexy" are selected as the evaluation items.

The process of creating a subspace corresponding to each of the evaluation items such as "feminine" and "cute" is described in the following with reference to FIG. 7. First of all, a subspace for an evaluation item such as "cute" is created by using a statistical learning process. For instance, when creating a subspace for "cute", the Gabor feature values or LBP feature values are extracted from M face images for learning, and, at the same time, a "cute" value y (label information; a rank value from 1 to 10, for instance, to indicate a higher level of being "cute" as the rank value is increased) based on a human subjective view is assigned.

When a feature value vectors corresponding to the feature values discussed earlier is extracted from the M face images for learning, a set of learning vector labels can be obtained.

$$\{(Xi, Yi), i=1, \ldots, M\} \quad \text{Eq(1)}$$

where the number of dimensions of the feature value vector x is N.

The feature value vector x typically consists of a high dimensional vector so that selecting only the important dimensions may be required (dimension reduction). When the feature value vector x does not include label information, the PCA (principle component analysis) is generally used. However, when the feature value vector x contains label information such as the "cute" value, the FDA (Fischer discriminant analysis) and the LFDA (local Fischer discriminant analysis) may also be useful.

These discriminant analysis techniques are performed by clustering the feature vectors x based on the label information and projecting the feature vectors x onto the low dimensional subspaces so as to minimize the within-class variance and maximize the between-class variance in each cluster. These low dimensional subspaces are referred to as subspaces within N dimensional spaces.

A projection matrix W is obtained from the set of vector labels (Eq. 1) by using a linear discriminant analysis, and is stored in the projection matrix/regression model storage unit 4e of the storage unit 4 in advance. This operation is executed for each and every evaluation item. In other words, the projection matrices W are generated by the same number as the number of the evaluation items based on human impressions. Each projection matrix W is used for projecting the feature values obtained from the synthesized face images onto the subspace corresponding to each evaluation item in step ST110. By projecting the feature values onto the subspaces, the feature values are plotted on the corresponding coordinates of the subspaces.

Steps ST101 to ST110 of program P1 were discussed above. In the following, for the convenience of description, the process executed by program P3 shown in FIG. 3 is described. In program P3, the target face image is received, and the feature values thereof are acquired.

In program P3, it is assumed that the target face image is acquired by using a camera unit including an image sensor not shown in the drawings. First of all, the target face image is acquired by a target face image input unit 20 consisting of a camera unit (step ST301). A face is detected in the obtained image, and it is determined if a face has been successfully detected (step ST302). If a face has not been successfully detected (no in step ST302), the parameters are adjusted (step ST303), and the capturing of the target face image is tried once again (step ST301). The process executed in steps ST301 to ST303 is similar to that of steps ST101 to ST103 of program P1, and the parameter adjustment may be performed similarly as in these program steps.

The acquired target face image is stored in memory (ST304) not shown in the drawings, and the feature values are extracted from the target face image and stored in memory (step 305). These feature values are treated as vectors to be projected onto the subspaces corresponding to the various evaluation items, and stored in memory (ST306). As the execution of step ST306 is possible only when the evaluation items are determined, step ST306 is executed only after the evaluation items are determined in step ST204 of program P2. Because the feature values, the evaluation items and the subspaces are similar to those discussed earlier in conjunction with step ST110, a detailed description thereof is omitted here. The process of program P3 is executed as discussed above, and the process is taken over by program P1 at connecting point A.

The target face image can be obtained from a wide range of sources as discussed above, and may vary in property to a significant extent depending on the illuminating condition at the time of image capturing. However, as the Gabor feature values or LBP feature values that are used in the first embodiment are localized statistical values, the influences of the illuminating conditions can be minimized.

In the following, the process in step ST111 and the subsequent steps of program P1 is described in the following, and reference is made to FIG. 7.

It should be noted in this conjunction that the coordinates (or the feature value vectors) in the feature value spaces of the target face image are obtained in step ST305 discussed above, and the coordinates are obtained by projecting (plotting) the feature value vectors of the target face image onto the subspaces corresponding to different evaluation items in step ST306.

In step ST111, with respect to the subspace for one of the evaluation items "cute", for instance, the Euclidian distance computation unit 29 picks out a vector P obtained by projecting the feature value vector of each synthesized face image of the user onto the subspace and a vector Q obtained by projecting the feature value vector of the single target face image onto the subspace, and the Euclidian distance d(P, Q) between these two vectors is computed by using Eq. 2 given below.

$$d(P, Q) = \sqrt{\sum_{i=1}^{n} (y_i - x_i)^2} \quad (2)$$

where n is the number of dimensions of the subspace, yi is the value of vector P on the i-th axis, and xi is the value of vector Q on the i-th axis.

More specifically, as shown in FIG. 7, the distance between the coordinates in the synthesized face image 1 and the target face image in the "cute" subspace is computed. The shorter the distance between them is, the similar the two face images are in the "cute" subspace. Similarly, in step ST111, the distance between the coordinates in the synthesized face image 1 and the target face image is computed in each of the "feminine" subspace, the "sexy" subspace and the "coquette" subspace. As a result of these processes, the degrees of similarity in terms of a plurality of predetermined evaluation items are computed for each synthesized face image.

The degree of similarity may consist of the Euclidian distance, and in this case, the more similar the two images are, the small the value of similarity becomes. As this is not intuitive for the user, the degree of similarity may be conformed to the intuition of the user by converting the value of similarity such that the value of similarly is 100 when the Euclidian distance is zero. In the following description, the similarity is considered to be higher as the Euclidean distance gets smaller.

The degree of similarly is thus computed for each and every evaluation item, and the "overall similarity" between each synthesized face image and the target face image may be give as an average value of the degrees of similarity for all of the evaluation items.

Then, in step ST112, it is determined if all of the foregoing processes have been completed for each and every evaluation item. If not (no in step ST112), the program flow returns to step ST109 where the next synthesized face image is obtained from the synthesized face image storage unit 4d, and the foregoing processes are repeated until the degrees of similarity between the target face image and all of the synthesized face images have been computed with respect to all of the evaluation items. Once the "overall similarity" between the target face image and all of the synthesized face images have been computed for all of the evaluation items (yes in step ST112), the make-up technique extraction unit 24 identifies the make-up technique (which is referred to as "optimum make-up technique" hereinafter) that gave rise to the synthesized face image demonstrating the highest degree of similarly to the target face image, and reads out the specific contents (names of the used cosmetic products and the procedures of applying such cosmetic products) of the optimum make-up technique from the make-up technique storage unit 4c to be stored in a prescribed memory region (step ST113). This concludes the flow of program P1.

The process in program P2 is described in the following. In the first embodiment, the evaluation items based on human impressions mentioned above are determined from the estimated gender and age of the user.

Program P2 is initiated only after a face detection has been successfully carried out (yes in step ST102). It is supposed that the face image of the user has been normalized. First of all, feature values are extracted from the face image of the user (step ST201). The gender and age can be estimated from the eyes, the mouth, the contour of the face and the wrinkles, and four directional features may be used as the feature values.

The attribute estimation model storage unit 4a is accessed to read out an attribute estimation model (step ST202). The process of generating an attribute estimation model is described in the following. For the simplification of the description, only the estimation of gender is described here. First of all, an attribute estimation model associated with "gender" is obtained in advance by means of a statistical learning process. When performing a learning process for the attribute estimation model, as discussed earlier in conjunction with the generation of subspaces, Gabor feature values or LBP feature values are extracted from M face images for learning, and at the same time, values y (label information) representing gender (female or male) based on human subjective judgment are attached to the face images for learning.

Thereafter, an attribute determination model for the output y (gender) for a given input is learned. The learning process may be based on such techniques as the linear discriminant analysis, the SVM (support vector machine) and the AdaBoost.

The face database that can be used for learning the attribute estimation model may consist of such per se known databases as the NIST (National Institute of Standards and Technology) and the FERET (the facial recognition technology). In particular, when the faces of Japanese females are of interest, the JAFFE (Japanese Female Facial Expression) database may be used.

The age and gender are then estimated (ST203). More specifically, the age and gender of the user can be directly obtained based on the feature values (feature value vector) extracted from the detected face image of the user. The attribute estimation model is typically formed as a mathematical function, and values for the age and gender are associated with the coordinates of the space defined by the attribute estimation model. Thus, by feeding the feature value vector into the attribute estimation model, the age and gender can be directly obtained.

Based on the age and gender obtained by accessing the attribute estimation model, the evaluation item storage unit 4b is accessed to determine the evaluation items that are going to be used for the determination of similarity, and the determined evaluation items are stored in a prescribed memory region (step ST204). The system may also be configured such that the evaluation items used for the determination of similarity may be freely selected by the user by using the user interface 6. Furthermore, the system may be configured such that the evaluation items for which rank values are to be produced may be freely selected. Thus, the process of program P2 is concluded. The stored evaluation items are referenced in step ST110, and the similarity is computed in the corresponding subspace.

The age and gender of the user are estimated from the received face image in the attribute estimation model discussed above. Additionally, the race (caucasoid, mongoloid and negroid) may be determined in a similar fashion, and the selection of the evaluation items may take into account the estimated race.

The structure and process for determining similarity between the target face image and the synthesized face images obtained by applying various make-up techniques to the face image of the user have been described. The functionality of the structure and process can be improved if, in addition to such similarities, the rank values of the target face image, the face image of the user without cosmetic operation and the face image of the user for whom the cosmetic operation is in progress, are determined on a real time basis.

Figure 9:
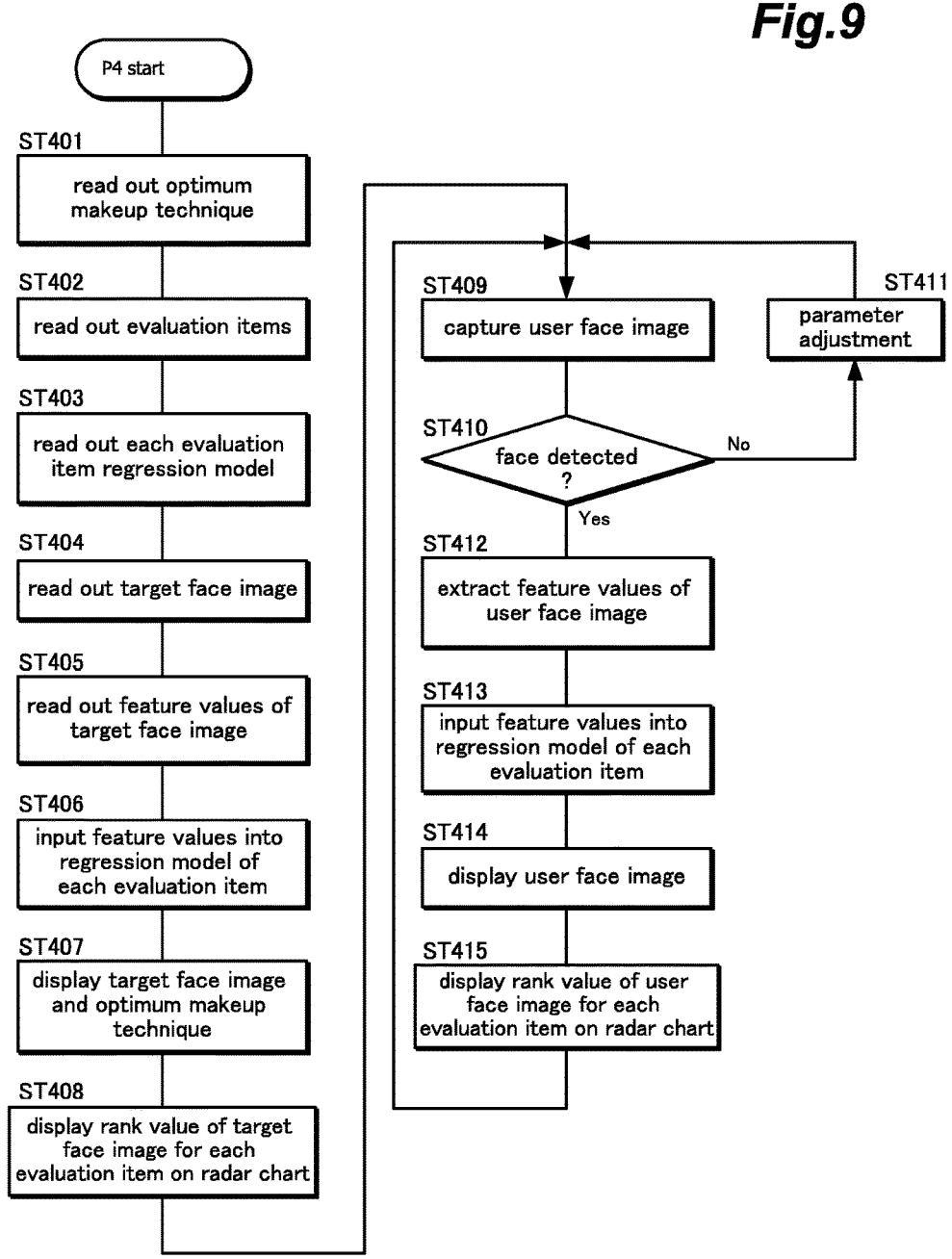
FIG. 9 is a flowchart showing the process of displaying rank values to the user in the cosmetic assist device.

FIG. 9 is a flowchart showing the process of displaying rank values to the user on the cosmetic assist device 1. Program P4 shown in this flowchart may be initiated either upon completion of program P1 discussed earlier in conjunction with FIG. 2, for instance, or manually by the user.

The process of displaying the rank values, the make-up techniques, the target face image and the user's face image on a real time basis is described in the following with reference to FIG. 9 and FIG. 1. The rank values are assigned by the evaluation unit 40.

The specific contents of the optimum make-up technique stored in step ST113 of program P1 are retrieved (step ST401). The evaluation items stored in step ST204 of program P2 or the evaluation items selected manually by the user are received (step ST402). The projection matrix/regression model storage unit 4e is accessed to read out the regression model for each evaluation item stored in the projection matrix/regression model storage unit 4e in advance (ST403).

The method of creating regression models is described in the following. The regression models in the subspaces corresponding to the various evaluation items (such as "feminine", "sexy" and "cute") are obtained by a statistical learning process. For instance, when learning the regression model for "cute", as discussed earlier as a process of creating subspaces, Gabor feature value or LBP feature values discussed earlier are extracted from M face images for learning process while the value y of "cute" (label information) according to a human subjective judgement is assigned to each face image.

The projection matrix J for the evaluation item "cute" is obtained by the linear discriminant analysis discussed above, and the regression model for the output y (rank value) for the input x is learned in the low dimensional space following the projection of the feature value vector thereon. The learning process may consist of linear regression, Bayesian linear regression, SVR (support vector regression), and so on. By using a regression model, the rank value can be estimated when an unknown feature value vector is received. In the first embodiment, it is also possible to use a neural network or the like, instead of a regression model, to estimate the rank value.

Based on the face image of the user, the feature value extraction unit 25 extracts feature values (feature value vector), and the subspace projection unit 26 generates a projection vector from the product of the projection matrix and the feature value vector. The rank estimation unit 41 directly produces the rank value for "cute", for instance, corresponding to the received feature values by accessing the regression model via the projection vector (coordinate). The regression model typically consists of a mathematical function, and the rank value of each evaluation item, such as "cute", is associated with the coordinate in the space defined by the regression model. Therefore, by multiplying the projection matrix J corresponding to each regression model to the feature value vector, and inputting the product to the regression model, the rank value for each evaluation item can be directly obtained. Thus, the subspace projection unit 26 is internally incorporated with the rank estimation unit 41, and functions as a regression model projection unit with the aid of the rank estimation unit 41.

The target face image which was stored in memory in step ST304 of program P3 discussed earlier is read out (step ST404). The feature values of the target face image which are stored in memory in step ST305 of program P3 is read out (step ST405). The read out feature values are fed to the regression model of each evaluation item by the subspace projection unit 26 (step ST406) to provide a rank value for the evaluation item. The data path for this process is not shown in FIG. 1. In practice, it is accomplished by the overall control unit 7 that reads out the feature values of the target face image from memory not shown in the drawings, and passes the feature values directly to the subspace projection unit 26.

The target face image read out in step ST404 and the specific contents of the optimum make-up technique read out in step ST401 are displayed on the display unit 5 (step ST407).

The rank value for each evaluation item in regard to the target face image (in particular the feature values thereof) read out in step ST404 is plotted on the radar chart displayed on the display unit 5 (step ST408).

The image of the user to whom the cosmetic operation is to be performed is captured by the camera unit 2 (step ST409).

Then, similarly as in step ST102, the face of the user is detected by the face detection unit 10, and it is determined if a face has been successfully detected (step ST410). If not (no in step ST410), the parameters for image capturing are adjusted (step ST411), and the image of the user is captured once again (ST409). If a face has been successfully detected, the feature value extraction unit 25 extracts the feature values of the face image of the user (step ST412). As the feature values to be extracted are no different from those used in step ST109 of program P1 discussed earlier, the detailed discussion on the feature values are omitted here. It is also possible to track the face region in the succeeding frames.

The subspace projection unit 26 multiplies the projection matrix J prepared for each evaluation item is multiplied to the feature value vector formed by the obtained feature values, and feed the product to the regression model (step ST413). By executing this procedure for each and every evaluation item, the current rank values (for the cosmetic operations in progress) of the user in regards to all of the evaluation items are extracted.

The face image of the user obtained in step ST409 is displayed on the display unit 5 (step ST414).

The rank value for each evaluation item obtained in step ST413 is plotted on the radar chart displayed on the display unit 5 (step ST415).

Upon completion of step ST415, after elapsing of a prescribed time period, the program flow returns to step ST409 to capture the face image of the user once again. Steps 409 to step ST419 form an endless loop, and the program may be configured that the program flow exits this loop upon detection of a key input from the user interface 6 during this prescribed time period. Owing to this loop of program steps, the camera unit 2 captures the image of the user repeatedly at a prescribed timing, and the evaluation unit 40 produces rank values for each renewed face image of the user. The display unit 5 then displays each renewed face image of the user and the rank values on a real time basis.

Figure 10C:
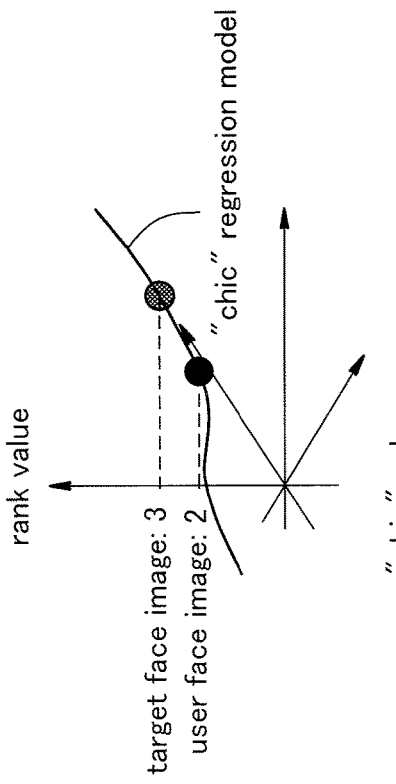
FIGS. 10a to 10c are diagrams showing the relationship between the subspaces corresponding to different evaluation items based on human impressions and the associated regression models.
Figure 10D:
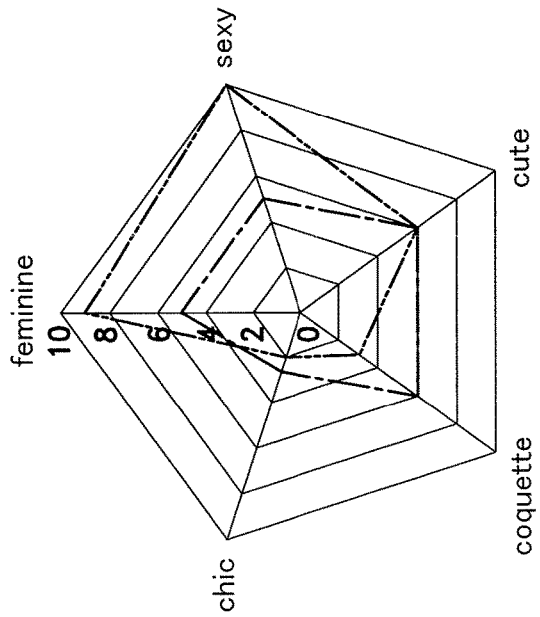
FIG. 10d is a diagram showing the rank values of the different evaluation items on a radar chart.
Figure 10A:
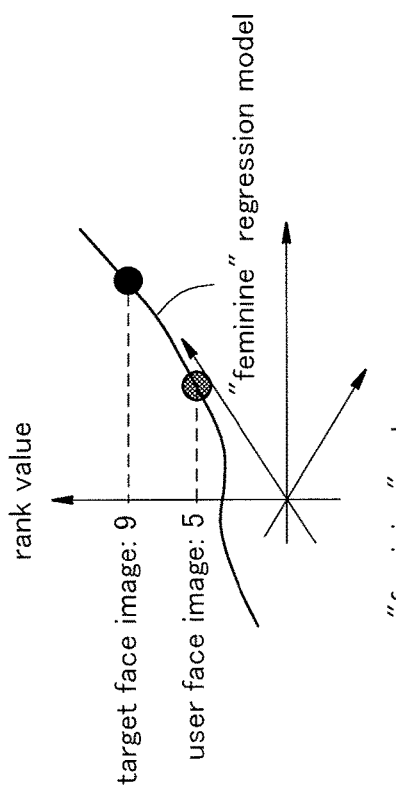
Figure 10B:
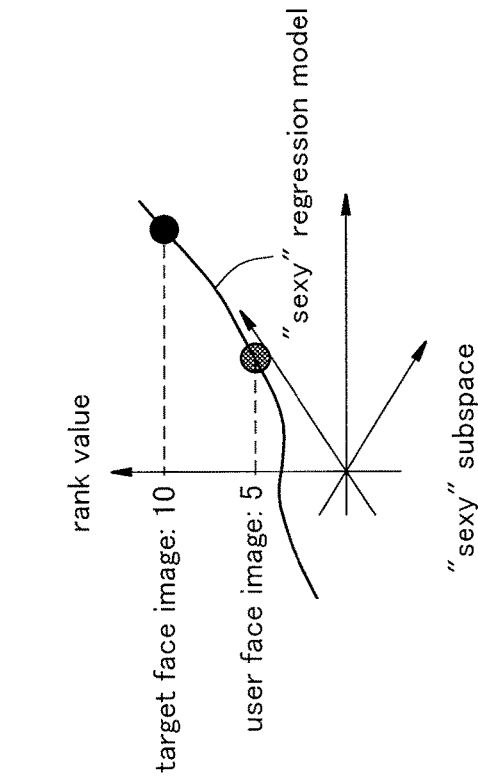

FIGS. 10a to 10c illustrate the relationship between the subspace corresponding to each evaluation item based on human impressions and the corresponding regression model, and FIG. 10d illustrates the radar chart on which the rank values for the various evaluation items are plotted.

FIG. 10a shows the relationship between the subspace for the evaluation item "feminine" and the regression model for "feminine" which is learned in this subspace, FIG. 10b shows the relationship between the subspace for the evaluation item "sexy" and the regression model for "sexy" which is learned in this subspace, and FIG. 10c shows the relationship between the subspace for the evaluation item "chic" and the regression model for "chic" which is learned in this subspace. In FIGS. 10a to 10c, three coordinate axes are shown in addition to the coordinate axis for representing the rank value, but, in practice, the subspace consists of a multi-dimensional space typically having numerous coordinate axes. In each of these diagrams, the regression models are represented by curves, but in reality should be represented by hyperplanes or hypersurfaces.

For the simplification of description, attention is drawn only to FIG. 10a. The black dot (of the two dots) on the curve represents the coordinate in the "feminine" subspace on which the feature values of the target face image are projected, and it shows that the rank value of this coordinate is nine. The gray dot on the curve represents the coordinate in the "feminine" subspace on which the feature values of the face image of the user are projected, and it shows that the rank value of this coordinate is five. FIGS. 10b and 10c should be viewed in a similar fashion. In other words, the rank values of the target face image and the user's face image can be determined by referencing the coordinate axis for the rank values.

The rank values obtained in this manner are plotted on a radar chart as shown in FIG. 10d. The radar chart is constructed such that the central part corresponds to lower rank values and the outer part corresponds to higher rank values, and the five radial axes correspond to the different evaluation items. In FIG. 10d, the rank values of the target face image for the different evaluation items are connected by a double-dot chain-dot line, and the rank values of the user's face image for the different evaluation items are connected by a single-dot chain-dot line.

As discussed earlier in conjunction with steps ST409 to ST415 of program P4, the face image of the user is periodically captured, and the rank value for each evaluation item is determined each time. Therefore, as the user progresses in cosmetic operation, and the face image of the user look more similar to the target face image, the rank value for each evaluation item on the radar chart shown in FIG. 10d grows greater (or smaller) in value, and the rank values of the user's face image may hopefully become substantially identical to those of the target face image. According to this scheme, even though the target face image is the aim or the desired result of the cosmetic operation, the rank value for each evaluation item may not be a maximum value, but a value determined by the corresponding regression model. It means that the standard for each evaluation item is determined as a value that can be achieved by a finite amount of learning process.

Therefore, the user is enabled to intuitively grasp the intended direction of the cosmetic operation (from the trend of the deviations in the radar chart). The user may select a target face image that has high rank values in regards to all of the evaluation items, but may also desire a cosmetic technique that achieves a high rank value on a certain subjective quality such as "cute" and "feminine" depending on the mood of the day. The cosmetic technique that is considered to be most desirable by the user may vary for various reasons on a day to day basis, and the present invention is able to cope with such a wide range of desires of the user.

Figure 11:
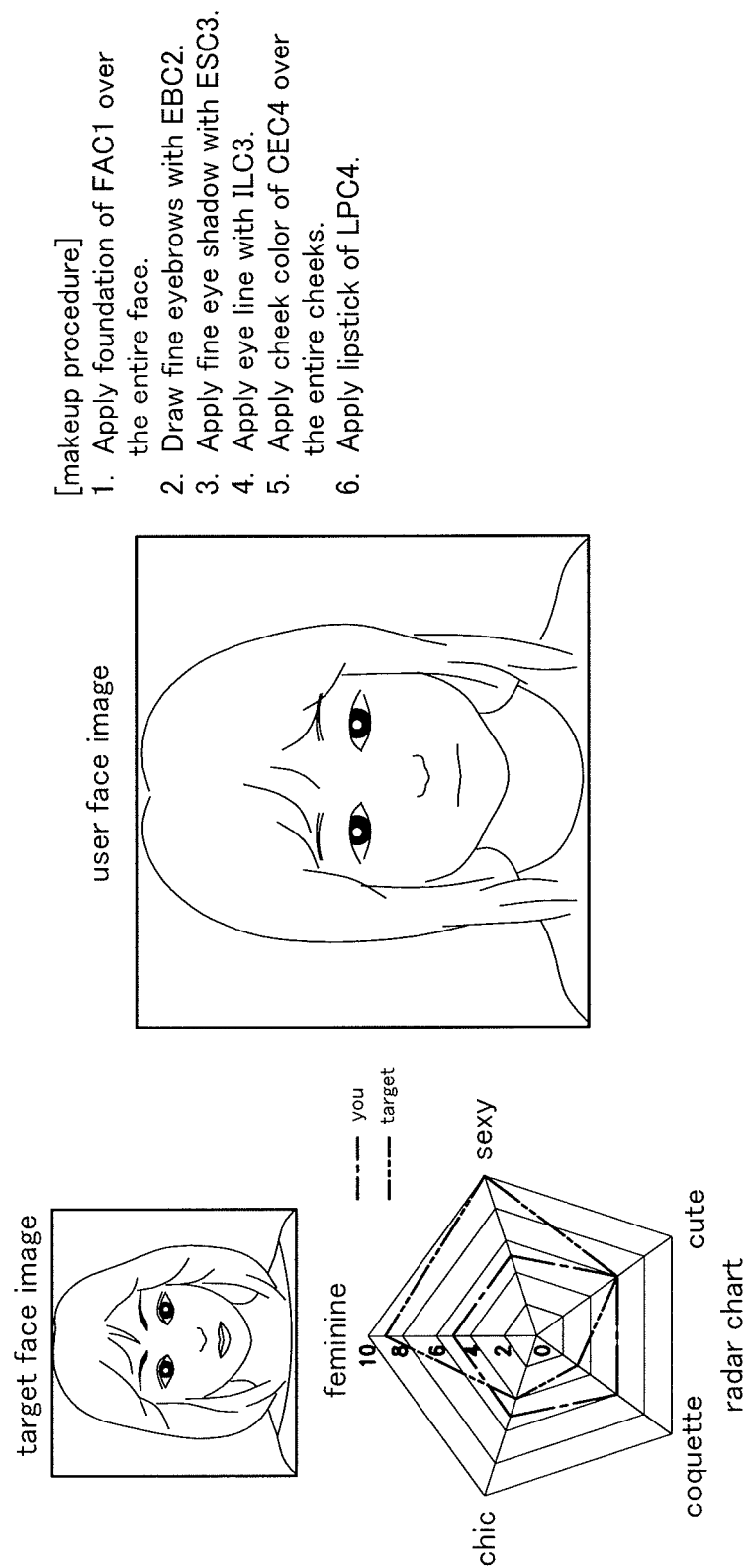
FIG. 11 is a view showing an example of the contents displayed on the display unit.

FIG. 11 is an example of the contents that are displayed on the display unit 5. As shown in FIG. 11, in the first embodiment, the display unit 5 displays the target face image obtained in step ST404 discussed earlier, the face image of the user obtained in step ST409, and the optimum make-up technique obtained in step ST401. In steps ST406 and step ST413, the rank values obtained by feeding the feature values to the regression models are plotted on the radar chart. In defining each make-up technique, not only the color symbols mentioned above but also the names of the cosmetic products that are used for achieving the colors represented by the color symbols may be displayed. When each synthesized face image is created in the detailed mode, the shapes of the eyebrow and the eye shadow may also be displayed.

As discussed earlier in conjunction with program P4, the face image of the user is periodically captured, and the rank values are plotted anew on the radar chart as soon as the face images are renewed on a real time basis.

The programs P1 to P4 discussed above may be distributed as application software that can be operated on hardware in the forms of portable terminals such as smartphones and tablets. The various components of the cosmetic assist device 1 may consist of various pieces of equipment incorporated in such smartphones and tablets. For instance, the camera unit 2 may consist of an internal camera incorporated in the terminal, the display unit 5 may consist of a display panel of the terminal consisting of organic EL or LCD, the target face image input unit 20 may consist of an internal camera or an interface for mounting a portable recording medium of the terminal, the image processing unit 3 may consist of the CPU and the peripheral system of the terminal, the storage unit 4 may consist of a mass storage device such as SSD (solid state drive) and a hard disk drive of the portable terminal.

Second Embodiment

Figure 12:
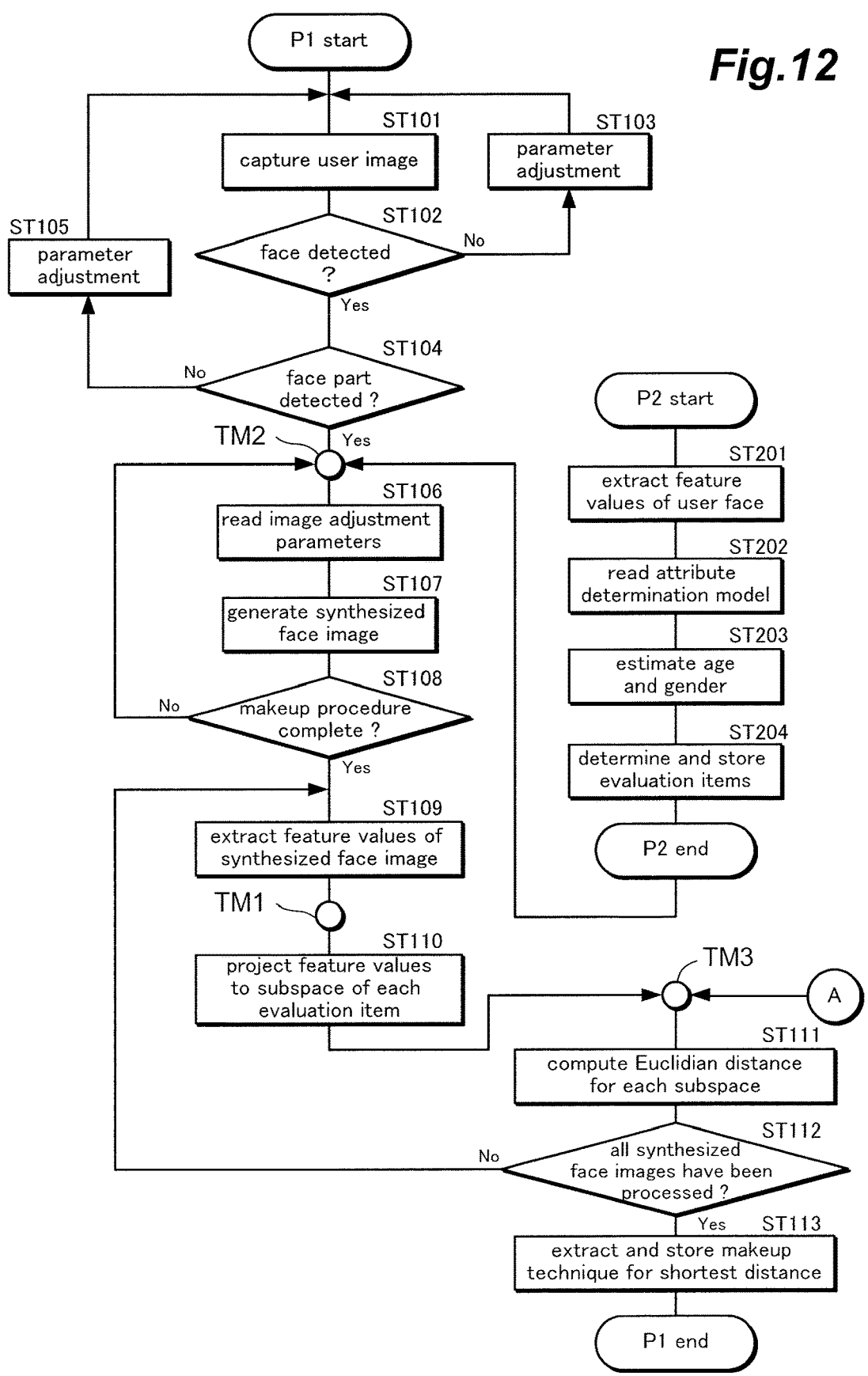
FIG. 12 is a flowchart showing the process of determining similarity in the cosmetic assist device of a second embodiment of the present invention.

FIG. 12 is a flowchart illustrating the process of determining similarity in the cosmetic assist device 1 of the second embodiment of the present invention. In the first embodiment, program P2 was constructed such that the process of program P2 is completed before the synchronization point TM1 provided between step ST109 and step ST110 is reached. On the other hand, in the second embodiment, program P2 is constructed such that the process of program P2 is completed before the synchronization point TM2 provided between step ST104 and step ST106 is reached.

As discussed earlier, program P1 allows the evaluation items to be determined by estimating the attributes of the user such as age and gender. In the second embodiment, the evaluation items are determined before a synthesized face image is generated. According to this process, the results of attribute estimation can be reflected in the generation of synthesized face images. As discussed earlier, an attribute such as race can be estimated in the attribute determination process. Cosmetic techniques using different sets of cosmetic products can be selected from the make-up technique storage unit 4c depending on the estimated race of the user so that more appropriate synthesized face images can be generated. As can be readily appreciated, the process of generating synthesized face images may be constructed such that different make-up techniques may be selected depending on the age and/or the gender of the user, as well as on the race of the user.

Figure 13:
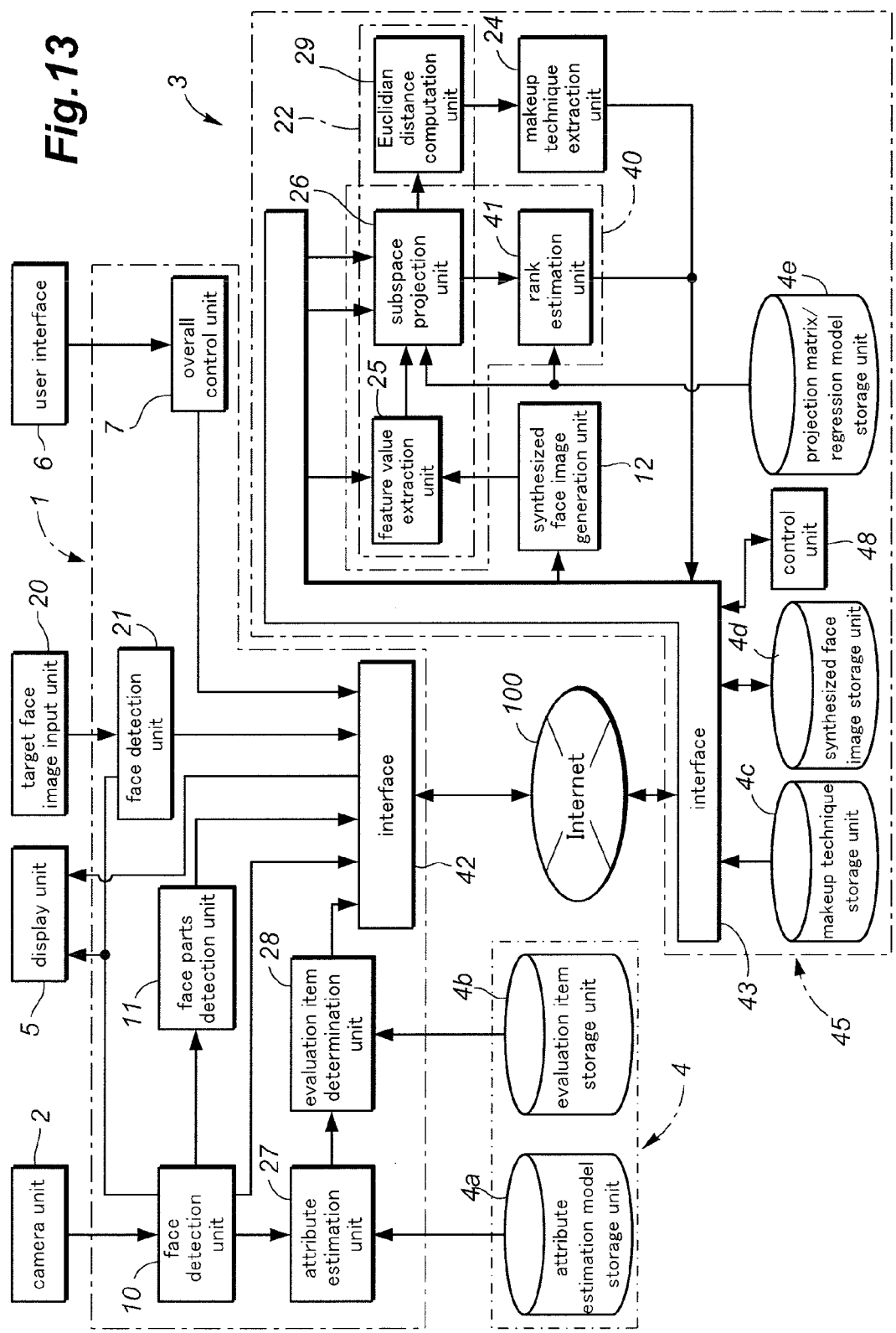
FIG. 13 is a block diagram showing the structure of the cosmetic assist device of a third embodiment of the present invention.

FIG. 13 is a block diagram showing the structure of the cosmetic assist device 1 according to the third embodiment of the present invention. In the first embodiment, the make-up technique storage unit 4c for storing make-up techniques that are to be used in the generation of synthesized face images, the synthesized face image storage unit 4d, the projection matrix/regression model storage unit 4e, the synthesized face image generation unit 12, the similarity determination unit 22, the rank estimation unit 41 and the make-up technique extraction unit 24 were all provided within the cosmetic assist device 1. However, the third embodiment differs from the first embodiment in that these components are provided outside of the cosmetic assist device 1.

As shown in FIG. 13, the cosmetic assist device 1 is provided with an interface 42 for establishing a link with an external network 100 such as the Internet. A server 45 (typically located remotely from the cosmetic assist device 1) is connected to this external network 100 via an interface 43. In other words, FIG. 13 shows a cosmetic assist system configured to make use of cloud computing. In this system, the main components of the image processing unit 3 discussed earlier is provided in the server 45.

The server 45 is provided with databases formed by a make-up technique storage unit 4c, a synthesized face image storage unit 4d and a projection matrix/regression model storage unit 4e. The server 45 is additionally provided with a similarity determination unit 22 consisting of a feature value extraction unit 25, a subspace projection unit 26 and a Euclidian distance computation unit 29, as well as a rank estimation unit 41 and a make-up technique extraction unit 24 associated with the similarity determination unit 22. The rank values produced by the rank estimation unit 41 and the optimum cosmetic technique produced by the make-up technique extraction unit 24 are forwarded to the cosmetic assist device 1 via the interface 43 of the server 45, the external network 100 and the interface 42, and displayed on the display unit 5. All of these components are entirely controlled by a control unit 48. As can be readily appreciated, all of these components can also be realized by the server as a computer system.

The data paths shown in FIG. 13 converge in the path passing through the interface 43, the external network 100 and the interface 43, but various pieces of image data before and after processing, and various parameters are exchanged between the various components similarly as in the embodiment illustrated in FIG. 1.

As discussed earlier in conjunction with the first embodiment, the synthesized face images are generated either in the simple mode or in the detailed mode. The number of the synthesized face images is great, 559,872 in the case of the detailed mode. The synthesized face images may remain the same as long as no new make-up technique is added, or no existing cosmetic technique is deleted or modified (or as long as no new cosmetic products that affect any cosmetic techniques are introduced). Therefore, the synthesized face image storage unit 4d typically consists of a referencing (read only) database.

However, in reality, the cosmetic products change with changes in fashion and/or seasons. Therefore, the control unit 48 may be configured to obtain new cosmetic product information via the external network 100, and reconstruct make-up techniques and update the contents of the make-up technique storage unit 4c by taking into account the obtained new cosmetic product information.

The synthesized face image storage unit 4d stores, in addition to the synthesized face images simulating various make-up techniques, the base face image (the face image of the user without any cosmetic technique applied thereto) serving as a base for image synthesis. When there are any change in the range of cosmetic products available on the market, the control unit 48 creates new synthesized face images by applying the updated cosmetic techniques to the base face image after asking for the acknowledgement of the user, and the new synthesized face images are stored in the synthesized face image storage unit 4d. Therefore, in such a case, the make-up technique storage unit 4c and the synthesized face image storage unit 4d consist of re-writable databases. By so doing, when the user desires to compare similarity to different target faces images, the need to generate synthesized face images each time is eliminated. It is also possible to store feature values extracted from the synthesized face images, instead of storing the synthesized images.

It is also possible to keep the synthesized face image storage unit 4d normally empty, and store the synthesized face images of the user in the synthesized face image storage unit 4d only when the user uses the cosmetic assist device. The synthesized face images stored in the synthesized face image storage unit 4d may be entirely discarded once the optimum make-up technique has been decided from the determination of similarity. By using the synthesized face image storage unit 4d in such a dynamic fashion, the need for the storage space of the synthesized face image storage unit 4d can be minimized.

In the third embodiment, because the server 45 for executing the image processing computation is separated from the cosmetic assist device, the processing jobs can be distributed over the network so that the risks such as those caused by the failure of databases can be distributed, and the cloud computing can be effectively utilized by shifting the computational load to the cloud computing.

As discussed above, in the third embodiment, the user is enabled to perform a cosmetic operation that allows the user's face to look similar to the target face image by using the constantly updated cosmetic products. By locating the databases and the hardware for executing the image processing computations remote from the cosmetic assist device 1, if the user possesses an information terminal such as a smartphone and a tablet, the user is enabled to receive the cosmetic assist service by connecting the information terminal to the server 45 via the external network 100.

Fourth Embodiment

FIG. 14 is a block diagram showing the structure of the cosmetic assist device 1 according to the fourth embodiment of the present invention. In the first embodiment, the similarity between the target face image and each of a plurality of synthesized face images generated by applying different cosmetic operations was determined by projecting the feature values from each pair of face images that are compared onto subspaces that corresponding to various evaluation items based on human impressions, and measuring the Euclidian distance between each pair of face images in each subspace. By feeding the feature values obtained from the target face image and the user's face images into the regression model for each evaluation item in the subspace projection unit 26, the rank value of each evaluation item was obtained. A primary feature of the fourth embodiment can be found in computing the similarity between the target face image and each synthesized face image feature value spaces.

In this embodiment, the process of generating synthesized face images from the combinations of the face image of the user captured by the camera unit 2 and various cosmetic techniques, and obtaining feature values from these synthesized face images, and the process of obtaining feature values from the target face image received by the target face image input unit 20 are similar to those of the first embodiment, and are therefore omitted from the following description.

As discussed in conjunction with the first embodiment, the feature values extracted from the synthesized face images and the target face image may be represented by multi-dimensional vectors. Therefore, it is also possible to directly pass the feature values extracted by the feature value extraction unit 25 to the Euclidian distance computation unit 29, without the intervention of the subspace projection unit 26, and compute the Euclidian distance between the two sets of feature values by using Eq. (2). Thereby, the degree of similarity between each synthesized face image and the target face image in the space of external appearance shown in FIG. 3 can be computed. By performing this process for each and every synthesized face image, the make-up technique extraction unit 24 is enabled to extract the make-up technique that achieved the synthesized face with the least distance to the target face image.

In this manner, in the fourth embodiment, the degree of similarity is determined from the overall external appearance without regard to the individual evaluation items so that the computational load can be reduced as compared to the case where the user selected a large number of evaluation items. Therefore, depending on the number of evaluation items that are taken into consideration, one can select either the feature spaces or the subspaces for the computation of similarity.

Even in this case, as the estimation of rank values based on the face image of the user and the target face image is performed independently by the subspace projection unit 26 and the rank estimation unit 41, no new restriction is imposed on the utilization of the cosmetic assist device 1.

The cosmetic assist device, the cosmetic assist system, the cosmetic assist method and the cosmetic assist computer program according to the present invention were described above in terms of the first to fourth embodiments. In the foregoing description, the synthetic face images having various different make-up techniques applied thereto and the target face images were given as exemplary objects for computing the degrees of similarity, and the face image of the user (when the cosmetic operation is in progress) and the target face image were given as exemplary objects for computing the rank values. However, the present invention is applicable not only to the field of performing make-up on the face of a user but also to other fields such as hairstyling and cosmetic surgery.

INDUSTRIAL APPLICABILITY

As the cosmetic assist system, the cosmetic assist method and the cosmetic assist computer program according to the present invention allow an optimum make-up technique to be extracted when a user tries to perform a cosmetic operation on her (or him), and can be implemented in various pieces of equipment such as a dedicated cosmetic assist device, a combination of a server and a terminal for providing a cosmetic assist service, and an information terminal such as a computer, a smartphone and a tablet incorporated with the cosmetic assist program.

GLOSSARY

1 cosmetic assist device
2 camera unit (image capturing unit)
3 image processing unit
4 storage unit
4a attribute estimation model storage unit
4b evaluation item storage unit
4c make-up technique storage unit
4d synthesized face image storage unit
4e projection matrix/regression model storage unit
5 display unit
6 user interface
7 overall control unit
10 face detection unit
11 face parts detection unit
12 synthesized face image generation unit
20 target face image input unit (input unit)
21 face detection unit
22 similarity determination unit
24 make-up technique extraction unit
25 feature value extraction unit
26 subspace projection unit (projection unit)
27 attribute estimation unit
28 evaluation item determination unit
29 Euclidian distance computation unit
40 evaluation unit
41 rank estimation unit
45 server

The invention claimed is:

1. A cosmetic assist device comprising:
a camera that captures a face image of a user;
a database that stores cosmetic techniques associated with image adjustment parameters including different colors;
a memory that stores instructions; and
a processor that executes the instructions stored in the memory to perform operations including:
receiving a target face image, which is different from the face image of the user captured by the camera;
generating a plurality of synthesized face images obtained by applying each of the cosmetic techniques on the face image of the user based on the image adjustment parameters associated with the cosmetic techniques in the database, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity; and
displaying the cosmetic technique that was extracted,
wherein the determining the degree of the similarity comprises:
extracting a feature value from each of the target face image and the plurality of synthesized face images to obtain a plurality of feature values, and
projecting each of the plurality of feature values onto a subspace corresponding to each of a plurality of different evaluation items; and
wherein a degree of similarity in the subspace is determined from a Euclidian distance between coordinates onto which the feature value obtained from each of the plurality of synthesized face images and the target face image are projected, and
the degree of similarity between the target face image and each of the plurality of synthesized face images is determined according to the degree of similarity in the subspace corresponding to each of the plurality of different evaluation items.

2. A cosmetic assist device comprising:
a camera that captures a face image of a user;
a database that stores cosmetic techniques associated with image adjustment parameters including different colors;
a memory that stores instructions; and
a processor that executes the instructions stored in the memory to perform operations including:
receiving a target face image, which is different from the face image of the user captured by the camera;
generating a plurality of synthesized face images obtained by applying each of the cosmetic techniques on the face image of the user based on the image adjustment parameters associated with the cosmetic techniques in the database, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity;

producing a rank value of a prescribed evaluation item for each of the face image of the user and the target face image; and a display that displays the rank value for each of the face image of the user and the target face image and the cosmetic technique that was extracted, wherein the producing the rank value comprises:

extracting a feature value from the target face image and each of the plurality of synthesized face images, to obtain a plurality of feature values;

projecting each of the plurality of feature values onto a subspace corresponding to each of a plurality of different evaluation items; and producing the rank value of the prescribed evaluation item according to coordinates of the plurality of feature values projected onto the subspace.

3. A cosmetic assist device comprising:

a camera that captures a face image of a user;

a database that stores cosmetic techniques associated with image adjustment parameters including different colors;

a memory that stores instructions; and a processor that executes the instructions stored in the memory to perform operations including:

receiving a target face image, which is different from the face image of the user captured by the camera;

generating a plurality of synthesized face images obtained by applying each of the cosmetic techniques on the face image of the user based on the image adjustment parameters associated with the cosmetic techniques in the database, the plurality of synthesized face images respectively including the different colors included in the image adjustment parameters stored in the database;

determining a degree of similarity between each synthesized face image, of the plurality of synthesized face images, and the target face image;

selecting a synthesized face image having a highest degree of similarity, from the plurality of synthesized face images;

extracting a cosmetic technique, of the cosmetic techniques, that was used to obtain the synthesized face image selected to have the highest degree of similarity;

producing a rank value of a prescribed evaluation item for each of the face image of the user and the target face image; and a display that displays the rank value for each of the face image of the user and the target face image and the cosmetic technique that was extracted, wherein the camera captures the face image of the user repeatedly at a prescribed timing, the processor produces the rank value for the face image of the user each time the camera captures the face image of the user, and the display displays the face image of the user and the rank value for the face image of the user each time the camera captures the face image of the user.

4. The cosmetic assist device according to claim 3, wherein the display displays the rank value on a radar chart having a plurality of coordinate axes, each corresponding to the prescribed evaluation item.

5. The cosmetic assist device according to claim 1, the processor, by performing the instructions stored in the memory, further estimating at least one of age or gender of the user from the face image of the user, wherein the subspace onto which the plurality of feature values are to be projected is determined according to the at least one of age or gender of the user estimated.

6. The cosmetic assist device according to claim 1, wherein the plurality of feature values are represented by an N-dimensional vector, and the subspace has a smaller number of dimensions than the N-dimensional vector.

7. The cosmetic assist device according to claim 1, wherein the database is a rewritable database.

8. The cosmetic assist device according to claim 7, further comprising:

a synthesized face image storage that stores the plurality of synthesized face images generated by the processor in the generating of the plurality of synthesized face images, wherein the processor, by executing the instructions stored in the memory, further generates a new synthesized face image when contents of the database have been updated, by applying an updated cosmetic technique to the face image of the user, and stores the new synthesized face image in the synthesized face image storage.

9. A cosmetic assist system, comprising:

a camera that captures a face image of a user;

a database that stores cosmetic techniques associated with image adjustment parameters including different colors;

a memory that stores instructions;

a processor that executes the instructions stored in the memory to perform operations including:

receiving a target face image, which is different from the face image of the user captured by the camera;

accessing the database to acquire the cosmetic techniques and the image adjustment parameters, and generating a plurality of synthesized face images obtained by applying each of the cosmetic techniques on the face image of the user by referencing the image adjustment parameters associated with the cosmetic techniques, the plurality of synthesized face images respectively including the different colors included in the image adjustment parameters stored in the database;

determining a degree of similarity between each synthesized face image, of the plurality of synthesized face images, and the target face image; and selecting a synthesized face image having a highest degree of similarity, from the plurality of synthesized face images;

extracting a cosmetic technique, of the cosmetic techniques, that was used to obtain the synthesized face image selected to have the highest degree of similarity; and displaying the cosmetic technique that was extracted, wherein the determining the degree of the similarity comprises:

extracting a feature value from each of the target face image and the plurality of synthesized face images to obtain a plurality of feature values, and projecting each of the plurality of feature values onto a subspace corresponding to each of a plurality of different evaluation items; and wherein a degree of similarity in the subspace is determined from a Euclidian distance between coordinates onto which the feature value obtained from each of the plurality of synthesized face images and the target face image are projected, and the degree of similarity between the target face image and each of the plurality of synthesized face images is determined according to the degree of similarity in the subspace corresponding to each of the plurality of different evaluation items.

10. A cosmetic assist system, comprising:
a camera that captures a face image of a user;
a database that stores cosmetic techniques associated with image adjustment parameters including different colors;
a memory that stores instructions;
a processor that executes the instructions stored in the memory to perform operations including:
receiving a target face image, which is different from the face image of the user captured by the camera;
accessing the database to acquire the cosmetic techniques and the image adjustment parameters, and generating a plurality of synthesized face images obtained by applying each of the cosmetic techniques on the face image of the user by referencing the image adjustment parameters associated with the cosmetic techniques, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity;
producing a rank value of a prescribed evaluation item for each of the face image of the user and the target face image; and
a display that displays the cosmetic technique that was extracted and the rank value for each of the face image of the user and the target face image,
wherein the producing the rank value comprises:
extracting a feature value from the target face image and each of the plurality of synthesized face images, to obtain a plurality of feature values;
projecting each of the plurality of feature values onto a subspace corresponding to each of a plurality of different evaluation items; and
producing the rank value of the prescribed evaluation item according to coordinates of the plurality of feature values projected onto the subspace.

11. A cosmetic assist method, comprising
storing, into a database, cosmetic techniques associated with image adjustment parameters including different colors;
capturing a face image of a user by a camera;
inputting a target face image, which is different from the face image of the user captured by the camera;
generating a plurality of synthesized face images obtained by applying each of the cosmetic techniques on the face image of the user based on the image adjustment parameters associated with the cosmetic techniques in the database, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity; and
presenting the cosmetic technique that was extracted on a display,
wherein the determining the degree of the similarity comprises:
extracting a feature value from each of the target face image and the plurality of synthesized face images to obtain a plurality of feature values, and
projecting each of the plurality of feature values onto a subspace corresponding to each of a plurality of different evaluation items; and
wherein a degree of similarity in the subspace is determined from a Euclidian distance between coordinates onto which the feature value obtained from each of the plurality of synthesized face images and the target face image are projected, and
the degree of similarity between the target face image and each of the plurality of synthesized face images is determined according to the degree of similarity in the subspace corresponding to each of the plurality of different evaluation items.

12. A cosmetic assist method, comprising:
storing, into a database, cosmetic techniques associated with image adjustment parameters including different colors;
capturing a face image of a user by a camera;
inputting a target face image, which is different from the face image of the user captured by the camera;
generating a plurality of synthesized face images obtained by applying each of the cosmetic techniques on the face image of the user based on the image adjustment parameters associated with the cosmetic techniques in the database, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity;
producing a rank value of a prescribed evaluation item for each of the face image of the user and the target face image; and
displaying the cosmetic technique that was extracted and the rank value for each of the face image of the user and the target face image,
wherein the producing the rank value comprises:
extracting a feature value from the target face image and each of the plurality of synthesized face images, to obtain a plurality of feature values;
projecting each of the plurality of feature values onto a subspace corresponding to each of a plurality of different evaluation items; and
producing the rank value of the prescribed evaluation item according to coordinates of the plurality of feature values projected onto the subspace.

13. A cosmetic assist device comprising:
a camera that captures a face image of a user;
a database that stores cosmetic techniques associated with image adjustment parameters including different colors;
a memory that stores instructions; and
a processor that executes the instructions stored in the memory to perform operations including:
receiving a target face image, which is different from the face image of the user captured by the camera;
generating a plurality of synthesized face images obtained by applying each of the cosmetic techniques on the face image of the user based on the image adjustment parameters associated with the cosmetic techniques in the database, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity; and
displaying the cosmetic technique that was extracted, wherein
the image adjustment parameters include facial parts associated with the different colors to be applied to the facial parts,
the processor, executing the instructions stored in the memory, extracts the facial parts from the face image of the user,
the plurality of synthesized face images are generated by applying the different colors on the facial parts of the face image of the user, the facial parts being associated with the different colors in the database.

14. The cosmetic assist device according to claim 13, wherein
the processor, executing the instructions stored in the memory, further perform operations including:
determining whether the facial parts are extracted from the face image of the user; and
causing the camera to recapture the face image of the user with different camera parameters, until the facial parts are extracted from the face image of the user.

15. A cosmetic assist method, comprising the
storing, into a database, cosmetic techniques associated with image adjustment parameters including different colors;
capturing a face image of a user by a camera;
inputting a target face image, which is different from the face image of the user captured by the camera;
generating a plurality of synthesized face images obtained by applying each of the cosmetic techniques on the face image of the user based on the image adjustment parameters associated with the cosmetic techniques in the database, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity; and
presenting the cosmetic technique that was extracted on a display,
wherein
the image adjustment parameters include facial parts associated with the different colors to be applied to the facial parts,
the method further comprises extracting the facial parts from the face image of the user,
the plurality of synthesized face images are generated by applying the different colors on the facial parts of the face image of the user, the facial parts being associated with the different colors in the database.

16. A cosmetic assist method, comprising:
storing, into a database, cosmetic techniques associated with image adjustment parameters including different colors;
capturing a face image of a user by a camera;
inputting a target face image, which is different from the face image of the user captured by the camera;
generating a plurality of synthesized face images obtained by applying each of the cosmetic techniques on the face image of the user based on the image adjustment parameters associated with the cosmetic techniques in the database, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity;
producing a rank value for a prescribed evaluation item for each of the face image of the user and the target face image; and
displaying the cosmetic technique that was extracted and the rank value for each of the face image of the user and the target face image,
wherein
the camera captures the face image of the user repeatedly at a prescribed timing,
the producing the rank value produces the rank value for the face image of the user each time the camera captures the face image of the user, and
the displaying displays the face image of the user and the rank value for the face image of the user each time the camera captures the face image of the user.

17. A cosmetic assist system, comprising:
a camera that captures a face image of a user;
a database that stores cosmetic techniques associated with image adjustment parameters including different colors;
a memory that stores instructions;
a processor that executes the instructions stored in the memory to perform operations including:
receiving a target face image, which is different from the face image of the user captured by the camera;

accessing the database to acquire the cosmetic techniques and the image adjustment parameters, and generating a plurality of synthesized face images obtained by applying each of the cosmetic techniques on the face image of the user by referencing the image adjustment parameters associated with the cosmetic techniques, the plurality of synthesized face images respectively including the different colors included in the image adjustment parameters stored in the database;

determining a degree of similarity between each synthesized face image, of the plurality of synthesized face images, and the target face image;

selecting a synthesized face image having a highest degree of similarity, from the plurality of synthesized face images;

extracting a cosmetic technique, of the cosmetic techniques, that was used to obtain the synthesized face image selected to have the highest degree of similarity;

producing a rank value of a prescribed evaluation item for each of the face image of the user and the target face image; and a display that displays the cosmetic technique that was extracted and the rank value for each of the face image of the user and the target face image, wherein the image adjustment parameters include facial parts associated with the different colors to be applied to the facial parts, the processor, executing the instructions stored in the memory, extracts the facial parts from the face image of the user, the plurality of synthesized face images are generated by applying the different colors on the facial parts of the face image of the user, the facial parts being associated with the different colors in the database.

18. A cosmetic assist system, comprising:
a camera that captures a face image of a user;
a database that stores cosmetic techniques associated with image adjustment parameters including different colors;
a memory that stores instructions;
a processor that executes the instructions stored in the memory to perform operations including:
receiving a target face image, which is different from the face image of the user captured by the camera;
accessing the database to acquire the cosmetic techniques and the image adjustment parameters, and generating a plurality of synthesized face images obtained by applying each of the cosmetic techniques on the face image of the user by referencing the image adjustment parameters associated with the cosmetic techniques, the plurality of synthesized face images respectively including the different colors included in the image adjustment parameters stored in the database;
determining a degree of similarity between each synthesized face image, of the plurality of synthesized face images, and the target face image;
selecting a synthesized face image having a highest degree of similarity, from the plurality of synthesized face images;
extracting a cosmetic technique, of the cosmetic techniques, that was used to obtain the synthesized face image selected to have the highest degree of similarity;
producing a rank value of a prescribed evaluation item for each of the face image of the user and the target face image; and
a display that displays the cosmetic technique that was extracted and the rank value for each of the face image of the user and the target face image,
wherein
the camera captures the face image of the user repeatedly at a prescribed timing,
the processor produces the rank value for the face image of the user each time the camera captures the face image of the user, and
the display displays the face image of the user and the rank value for the face image of the user each time the camera captures the face image of the user.

* * * * *